(12) United States Patent
Okamoto

(10) Patent No.: US 12,376,743 B2
(45) Date of Patent: Aug. 5, 2025

(54) OPHTHALMIC DEVICE

(71) Applicant: Tomey Corporation, Nagoya (JP)

(72) Inventor: Keiichiro Okamoto, Nagoya (JP)

(73) Assignee: Tomey Corporation, Nagoya (JP)

( * ) Notice: Subject to any disclaimer, the term of this patent is extended or adjusted under 35 U.S.C. 154(b) by 375 days.

(21) Appl. No.: 17/941,099

(22) Filed: Sep. 9, 2022

(65) Prior Publication Data

US 2023/0079050 A1  Mar. 16, 2023

(30) Foreign Application Priority Data

Sep. 10, 2021 (JP) .................................. 2021-148097

(51) Int. Cl.
| | |
|---|---|
| *G06K 9/00* | (2022.01) |
| *A61B 3/00* | (2006.01) |
| *A61B 3/10* | (2006.01) |
| *A61B 3/117* | (2006.01) |
| *A61B 3/12* | (2006.01) |
| *A61B 3/103* | (2006.01) |

(52) U.S. Cl.
CPC ............ *A61B 3/102* (2013.01); *A61B 3/0058* (2013.01); *A61B 3/1005* (2013.01); *A61B 3/117* (2013.01); *A61B 3/12* (2013.01); *A61B 3/103* (2013.01)

(58) Field of Classification Search
None
See application file for complete search history.

(56) References Cited

U.S. PATENT DOCUMENTS

| | | | |
|---|---|---|---|
| 8,931,904 B2* | 1/2015 | Torii | A61B 3/12 |
| | | | 351/205 |
| 9,125,593 B2* | 9/2015 | Isogai | A61B 3/12 |
| 9,554,700 B2* | 1/2017 | Nakahara | A61B 3/102 |
| 9,681,803 B2* | 6/2017 | Isogai | A61B 3/117 |
| 9,848,769 B2* | 12/2017 | Miyasa | G06V 40/19 |
| 10,022,047 B2* | 7/2018 | Yamashita | A61B 3/10 |
| 10,082,868 B2* | 9/2018 | Lu | G06V 40/19 |
| 10,213,101 B2* | 2/2019 | Uhlhorn | A61B 3/1173 |

(Continued)

FOREIGN PATENT DOCUMENTS

| | | |
|---|---|---|
| CN | 104146681 B | 11/2015 |
| CN | 111265183 A | 6/2020 |

(Continued)

*Primary Examiner* — Feng Niu
(74) *Attorney, Agent, or Firm* — Shumaker, Loop & Kendrick, LLP

(57) ABSTRACT

An ophthalmic device includes a first light source configured to output first light, a second light source configured to output second light, a first interferometer configured to acquire a first tomographic image of a first range based on first interference light, a second interferometer configured to acquire a second tomographic image of a second range based on second interference light, and a controller. The controller may be configured to perform a specific scan on a subject eye that scans the first light and the second light simultaneously in a same plane, wherein the first tomographic image and the second tomographic image are obtained by performing the specific scan, calculate an amount of distortion of the first tomographic image, correct the first tomographic image based on the amount of distortion, and correct the second tomographic image based on the amount of distortion.

7 Claims, 27 Drawing Sheets

(56) References Cited

U.S. PATENT DOCUMENTS

| | | | | |
|---|---|---|---|---|
| 10,251,548 B2* | 4/2019 | Sekiguchi | | A61B 3/1005 |
| 10,912,458 B2* | 2/2021 | Okamoto | | A61B 3/102 |
| 11,185,221 B2* | 11/2021 | Saika | | A61B 3/12 |
| 11,311,191 B2* | 4/2022 | Yamanari | | A61B 3/102 |
| 11,659,992 B2* | 5/2023 | Okamoto | | A61B 3/117 |
| | | | | 351/221 |
| 11,717,156 B2* | 8/2023 | Birkner | | A61B 3/102 |
| | | | | 351/206 |
| 12,076,087 B2* | 9/2024 | Yokoyama | | G06V 40/171 |
| 12,087,001 B2* | 9/2024 | Iwase | | G06T 7/33 |
| 2011/0090458 A1* | 4/2011 | Sakagawa | | A61B 3/102 |
| | | | | 351/246 |
| 2012/0083667 A1* | 4/2012 | Isogai | | A61B 3/14 |
| | | | | 600/300 |
| 2012/0113390 A1* | 5/2012 | Torii | | A61B 3/102 |
| | | | | 351/208 |
| 2012/0127428 A1* | 5/2012 | Isogai | | A61B 3/102 |
| | | | | 351/206 |
| 2012/0200859 A1 | 8/2012 | Breitenstein et al. | | |
| 2014/0085606 A1* | 3/2014 | Miyasa | | A61B 3/1005 |
| | | | | 351/206 |
| 2014/0211157 A1* | 7/2014 | Nakahara | | A61B 3/102 |
| | | | | 351/246 |
| 2015/0327762 A1 | 11/2015 | Isogai et al. | | |
| 2017/0027438 A1 | 2/2017 | Uhlhorn et al. | | |
| 2017/0202453 A1* | 7/2017 | Sekiguchi | | G06T 11/003 |
| 2017/0293354 A1* | 10/2017 | Lu | | G06V 20/64 |
| 2018/0279872 A1 | 10/2018 | Okamoto et al. | | |
| 2019/0355466 A1* | 11/2019 | Sugiyama | | G06T 7/0012 |
| 2020/0085292 A1 | 3/2020 | Fukuma et al. | | |
| 2020/0093363 A1* | 3/2020 | Saika | | A61B 5/0066 |
| 2020/0100674 A1 | 4/2020 | Yamanari et al. | | |
| 2021/0019493 A1* | 1/2021 | Yokoyama | | A61B 3/113 |
| 2021/0045631 A1* | 2/2021 | Birkner | | G06V 40/19 |
| 2022/0335633 A1* | 10/2022 | Iwase | | A61B 3/1225 |

FOREIGN PATENT DOCUMENTS

| | | |
|---|---|---|
| JP | 2012-075640 A | 4/2012 |
| JP | 2020044027 A | 3/2020 |
| JP | 2020054480 A | 4/2020 |

* cited by examiner

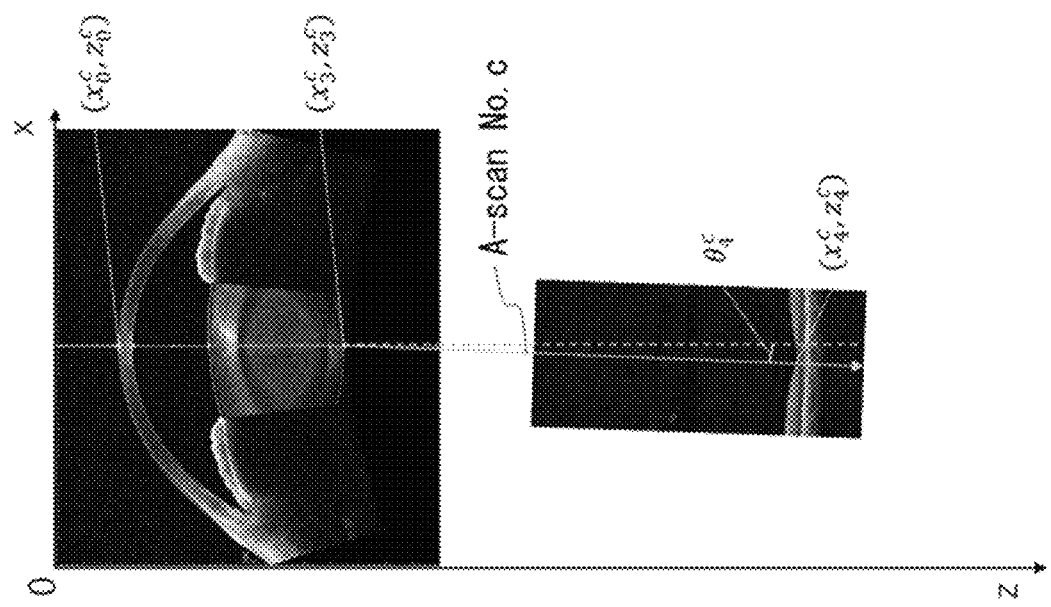
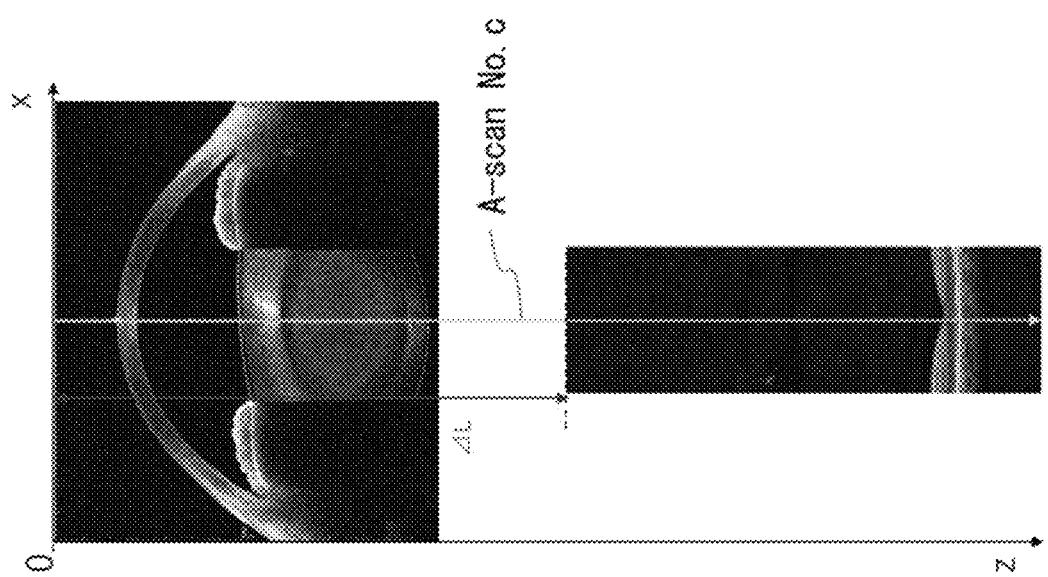

OPHTHALMIC DEVICE

CROSS-REFERENCE TO RELATED APPLICATION

This application claims priority to Japanese Patent Application No. 2021-148097, filed on Sep. 10, 2021, the entire contents of which are incorporated herein by reference.

TECHNICAL FIELD

The art disclosed herein relates to an ophthalmic device.

BACKGROUND

An ophthalmic device configured to acquire tomographic images for respective measurement ranges of a subject eye is in development. For example, an ophthalmic device of Japanese Patent Application Publication No. 2012-75640 is configured to acquire tomographic images of an anterior segment and of a fundus of a subject eye. This ophthalmic device includes an anterior segment light source and a fundus light source with a different wavelength from the anterior segment light source. In JP 2012-75640 A, the tomographic images in the respective ranges can be acquired by switching these light sources in accordance with each of the measurement ranges.

SUMMARY

A subject eye has unique curvatures, thicknesses, and refractive indexes at its different parts, thus a traveling direction of light may be refracted depending on a position of incident of the light entering the subject eye. Due to this, a distortion may occur in an acquired tomographic image of the subject eye. Further, in Japanese Patent Application Publication No. 2012-75640, since the respective tomographic images of the different measurement ranges of the subject eye are acquired separately, problems such as decreased measurement accuracy due to a state of the subject eye changing during measurement could arise. As such, complicated processing is required to acquire tomographic images with high correlation by correcting distortions and positional displacements between the tomographic images.

Further, in Japanese Patent Application Publication No. 2012-75640, if an optical system in which light travels through a same optical path in an anterior segment scan and a fundus scan is employed when a tomographic image of the anterior segment and a tomographic image of the fundus are to be acquired simultaneously by scanning light, it is difficult to scan a wide range encompassing the anterior segment and the fundus by light irradiated in each scan. Thus, in this case, an optical system in which the light travels through different optical paths in those scans needs to be employed. Specifically, for example, a telecentric scan needs to be employed for the anterior segment and a concentric scan forming a pivot point at a pupil needs to be employed for the fundus. In this case, due to the difference in the scanning configurations for the anterior segment and the fundus, a displacement may occur in coordinate systems of acquired tomographic images, and further distortion(s) in the tomographic images caused by a difference in incident angles of light to respective parts in the subject eye may occur. The description herein provides an art configured to acquire tomographic images with high correlation by correcting tomographic images acquired for different measurement ranges in a subject eye with a simple method.

An ophthalmic device disclosed herein may comprise: a first light source configured to output first light with which a subject eye is irradiated; a second light source configured to output second light with which the subject eye is irradiated; a first interferometer configured to acquire a first tomographic image of a first range of the subject eye based on first interference light obtained from reflected light of the first light; a second interferometer configured to acquire a second tomographic image of a second range of the subject eye based on second interference light obtained from reflected light of the second light, the second range being different from the first range; and a controller. The controller may be configured to: perform a specific scan on the subject eye that scans the first light and the second light simultaneously in a same plane, wherein the first tomographic image and the second tomographic image are obtained by performing the specific scan; calculate an amount of distortion of the first tomographic image; correct the first tomographic image based on the amount of distortion of the first tomographic image; and correct the second tomographic image based on the amount of distortion of the first tomographic image.

As described above, a subject eye has unique curvatures, thicknesses, and refractive indexes at its different parts, thus tomographic images acquired based thereon may have different shapes from that of the actual subject eye. In the ophthalmic device as above, the controller firstly calculates the amount of distortion of the first tomographic image and corrects the first tomographic image. Here, in this ophthalmic device, the first light and the second light are scanned simultaneously in the same plane. Due to this, each of the acquired first and second tomographic images is an image showing a cross section in the same plane of the subject eye. That is, the amount of distortion of the first tomographic image is a factor related to correction of the second tomographic image. As such, the second tomographic image can be corrected based on the amount of distortion of the first tomographic image. As such, in this ophthalmic device, not only the first tomographic image but also the second tomographic image can be corrected by calculating the amount of distortion of the first tomographic image.

BRIEF DESCRIPTION OF DRAWINGS

FIG. 22A is a diagram for explaining processes of correcting tomographic images of the fundus.

FIG. 22B is a diagram for explaining processes of correcting tomographic images of the fundus.

DETAILED DESCRIPTION

Figure 1:
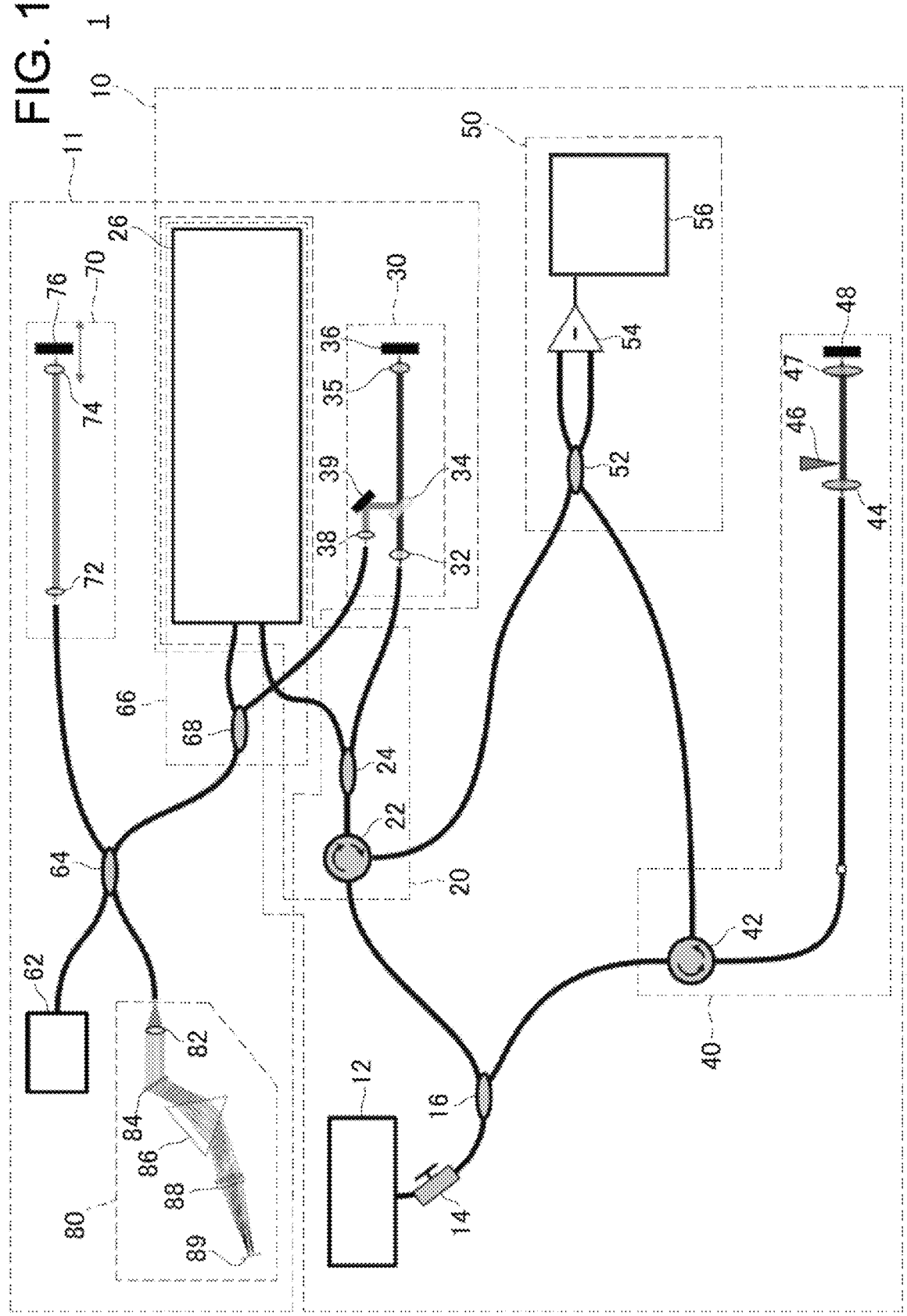
FIG. 1 is a schematic configurational diagram of an anterior segment OCT interferometer and a fundus OCT interferometer in an ophthalmic device of an embodiment.

Representative, non-limiting examples of the present disclosure will now be described in further detail with reference to the attached drawings. This detailed description is merely intended to teach a person of skill in the art further details for practicing preferred aspects of the present teachings and is not intended to limit the scope of the present disclosure. Furthermore, each of the additional features and teachings disclosed below may be utilized separately or in conjunction with other features and teachings to provide improved ophthalmic devices, as well as methods for using and manufacturing the same.

Moreover, combinations of features and steps disclosed in the following detailed description may not be necessary to practice the present disclosure in the broadest sense, and are instead taught merely to particularly describe representative examples of the present disclosure. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Some of the technical elements disclosed herein will be listed below. The respective technical elements as below are each independently useful.

In an embodiment of the present technology, a first optical path of the first light and a second optical path of the second light may partially overlap, an ophthalmic device may further comprise a scanner configured to scan the first light and the second light and arranged in an overlapping section where the first optical path and the second optical path partially overlap. The controller may be configured to perform the specific scan using the scanner.

According to such a configuration, the scanner for scanning the first light and the scanner for scanning the second light can be shared. Due to this, an internal configuration of the ophthalmic device can be suppressed from becoming complicated, and the number of components can be reduced. Further, as compared to a case of having separate scanners for scanning the first light and the second light, scanner synchronization upon measuring the subject eye is not necessary, thus control of the scanner is facilitated.

In an embodiment of the present technology, the controller may be configured to perform the specific scan a plurality of times on the subject eye so that the first light and the second light pass through a specific position of the subject eye, and perform respective specific scans radially at different positions in a circumferential direction with the specific position of the subject eye being a center.

According to such a configuration, the specific scan with the specific position as its center is performed in multiple radial angles (that is, multiple angular positions in the circumferential direction with the specific position as the center). That is, tomographic images in multiple cross sections can be acquired, and the tomographic images of the subject eye can be acquired three-dimensionally.

In an embodiment of the present technology, an ophthalmic device may further comprise a lens arranged between the scanner and the subject eye. The first range may include an anterior segment of the subject eye. The scanner may be configured to change an incident position of the first light outputted from the first light source on the subject eye. The first light may be scanned by the scanner so that traveling directions of the first light entering the subject eye are substantially parallel to each other.

According to such a configuration, the first light can suitably be scanned in the anterior segment of the subject eye. Further, since rays of light that are substantially parallel to each other enter the anterior segment of the subject, first tomographic images with less distortion can be acquired.

In an embodiment of the present technology, the second range may include a fundus of the subject eye. The scanner may be configured to change an incident position and an incident angle of the second light outputted from the second light source on the subject eye. The second light may be scanned by the scanner so that traveling directions of the second light entering the subject eye intersect between the scanner and the subject eye and are substantially parallel to each other inside the subject eye. In the description herein, "traveling directions of the second light entering the subject eye intersect between the scanner and the subject eye" means that each of the traveling directions of the second light, of which scanning position by the scanner (scan angle) is different when the second light is scanned, intersects each other between the scanner and the subject eye.

According to such a configuration, the second light can suitably be scanned in the fundus of the subject eye. Further, since the rays of light that became substantially parallel within the subject eye enter into the fundus of the subject eye, the second motographic image with less distortion can be acquired.

In an embodiment of the present technology, the controller may be configured to calculate respective incident positions and incident angles of the first light at a plurality of parts included in the first range of the subject eye in the specific scan, and calculate the amount of distortion of the first tomographic image based on the respective incident positions and incident angles and respective refractive indexes of the plurality of the parts.

The rays of light inputted to the anterior segment are parallel to a lens optical axis. Due to this, in the above configuration, the amount of distortion in the first tomographic image can be calculated with high accuracy based on the incident positions and incident angles of the plurality of parts (such as cornea and crystalline lens) included in the first range and the refractive indexes thereof.

In an embodiment of the present technology, the controller may be configured to perform the specific scan on the subject eye so that the first light and the second light pass through a specific position on the subject eye, and correct the second tomographic image based on the amount of distortion of the first tomographic image calculated based on the first light having entered the specific position.

In such a configuration, since the first optical path (axis) and the second optical path (axis) of light entering the specific position coincide with each other, the second tomographic image can suitably be corrected by using the amount of distortion calculated based on the first light having entered the specific position.

In an embodiment of the present technology, the controller may be configured to calculate a position of a specific part of the subject eye from the second tomographic image, and specify a gaze direction of the subject eye based on the position of the specific part.

In such a configuration, by calculating the position of the specific part in the second tomographic image, the gaze direction of the subject eye can be specified based on the light irradiated to this specific part.

In an embodiment of the present technology, the controller may be configured to calculate an angle between an optical axis of light passing through the specific position and the specified gaze direction.

In such a configuration, a degree of gaze displacement of the subject eye can be specified.

In an embodiment of the present technology, the controller may be configured to calculate an axial length of the subject eye based on the corrected first tomographic image and the corrected second tomographic image.

In such a configuration, the highly accurate eye axial length can be calculated.

Embodiment

Hereinbelow, an ophthalmic device 1 of an embodiment will be described. As shown in FIG. 1, the ophthalmic device 1 comprises an anterior segment OCT interferometer 10 configured to capture tomographic images of an anterior segment of a subject eye E and a fundus OCT interferometer 11 configured to capture tomographic images of a fundus of the subject eye E.

The anterior segment OCT interferometer 10 is used to capture tomographic images of the anterior segment of the subject eye E by optical coherence tomography. The anterior segment OCT interferometer 10 employs a Fourier domain scheme which performs light wave interference in a Fourier space, and especially uses swept-source OCT (SS-OCT) which captures tomographic images of the anterior segment of the subject eye E by detecting a spectrum interference signal using a wavelength scanning light source that scans light while changing its wavelength over time. As the wavelength scanning light source, for example, an external resonator-type wavelength sweeping light source that uses a wavelength-changing filter such as a diffraction grating and a prism, or various types of external resonator-type light source that uses a resonator-length changing Fabry-Perot tunable filter. Further, for example, a wavelength changeable DBR (Distributed Bragg Reflector) laser or a wavelength changeable surface emitting laser (VCSEL (Vertical Cavity Surface Emitting Laser)) that uses a MEMS (Micro Electro Mechanical Systems) mechanism may be used. Shapes of respective parts of the anterior segment of the subject eye E (such as a cornea, an anterior chamber, and a crystalline lens) can be measured from the tomographic images captured by the anterior segment OCT interferometer 10. The anterior segment OCT interferometer 10 is not limited to SS-OCT, and it may adopt, for example, another OCT using the Fourier domain scheme (such as spectrum domain OCT) or a scheme other than the Fourier domain scheme (such as time domain scheme).

As shown in FIG. 1, the anterior segment OCT interferometer 10 comprises an anterior segment light source 12, a measurement optical system 20, a calibration optical system 30, a reference optical system 40, and an interference optical system 50.

The anterior segment light source 12 is a wavelength sweeping light source, and a wavelength (wave number) of light outputted therefrom changes with a predetermined period. The anterior segment light source 12 is configured to output light with a long wavelength and is capable of outputting light with a central wavelength of 0.95 μm or more and 1.80 μm or less, for example. In the present embodiment, the anterior segment light source 12 outputs light with a central wavelength of 1.31 μm. When light with a long wavelength is used, it becomes easier for the light to pass through strong-scattering tissues such as opacity of the crystalline lens, a ciliary body, a conjunctiva, and a sclera, and further, due to its large absorbance by water, the light is less likely to reach the fundus, which allows stronger light to be irradiated. Due to this, by outputting the light with the central wavelength of 0.95 μm or more from the anterior segment light source 12, the chance of the light reaching the tissues constituted of scattering substances can be increased. Further, since the light with the central wavelength of 0.95 μm or more and 1.80 μm or less is not dispersed much by water, anterior segment OCT images with high image quality can be acquired by irradiating the subject eye E with the light within this range. Further, by outputting the light with the central wavelength of 1.80 μm or less from the anterior segment light source 12, a target site can be measured with high sensitivity by an indium/gallium/arsenic (InGaAs)-based light receiving element. Thus, by outputting the light of 0.95 μm or more and 1.80 μm or less from the anterior segment light source 12, the tomographic images of the anterior segment of the subject eye E can suitably be captured.

The anterior segment light source 12 has a polarization controller 14 and an optical coupler 16 connected thereto. Thus, the light outputted from the anterior segment light source 12 is inputted to the optical coupler 16 through the polarization controller 14 and is split in the optical coupler 16 into measurement light and reference light, for example, at a ratio of 9:1, and these lights are inputted respectively to the measurement optical system 20 and the reference optical system 40.

The measurement optical system 20 comprises an optical circulator 22, an optical coupler 24, and a probe optical system 26. The measurement light inputted to the measurement optical system 20 from the anterior segment light source 12 is inputted to the optical circulator 22. The measurement light inputted to the optical circulator 22 is inputted to the optical coupler 24 and is split in the optical coupler 24, for example, at a ratio of 99:1, and these lights are inputted respectively to the probe optical system 26 and the calibration optical system 30.

The probe optical system 26 comprises an anterior segment OCT optical system (FIG. 2) configured to capture tomographic images of the anterior segment of the subject eye E, a fundus OCT optical system (FIG. 4) configured to capture tomographic images of the fundus of the subject eye E, a refractometric measurement optical system (FIG. 6) configured to measure a refractivity of the subject eye E, a front monitoring optical system, a position detection light floodlighting optical system, a position detection light receiving optical system, a gaze fixing target optical system, an alignment optical system (not shown) configured to align the ophthalmic device 1 in a predetermined positional relationship with the subject eye E, and an observation optical system (not shown) configured to observe the subject eye E. Since configurations that were conventionally known can be used as the alignment optical system and the observation optical system, detailed descriptions thereof will be omitted.

Figure 2:
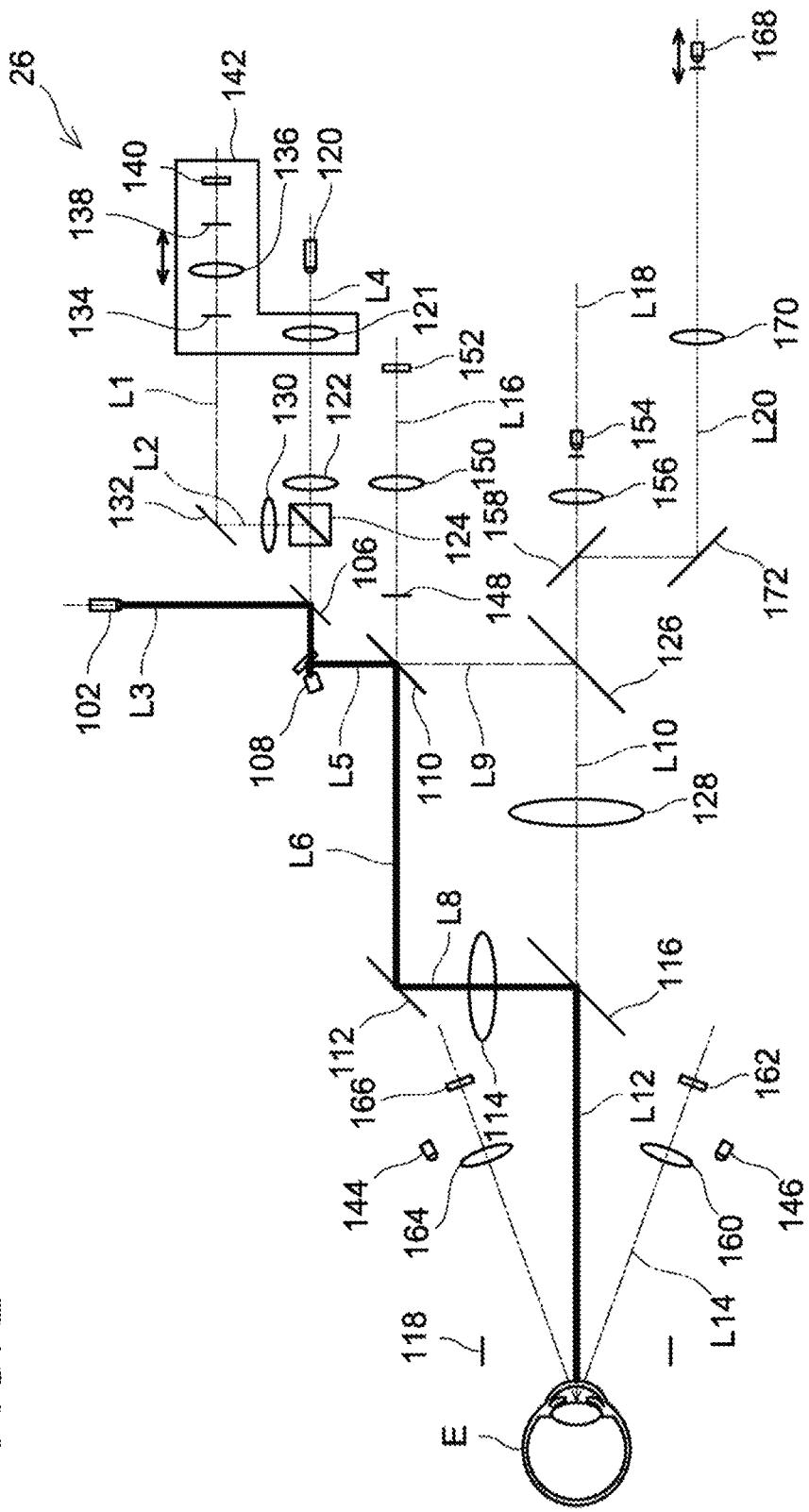
FIG. 2 is a diagram for explaining an anterior segment OCT optical system of the ophthalmic device of the embodiment.

As shown in FIG. 2, the anterior segment OCT optical system is composed of a fiber collimator 102, a dichroic mirror 106, a two-dimensional scanner 108, a dichroic mirror 110, a total reflection mirror 112, an objective lens 114, and a dichroic mirror 116. The dichroic mirrors 106, 110, 116 are each configured to reflect light with wavelengths longer than 0.90 μm and allow light with wavelengths shorter than 0.90 μm to penetrate.

Light inputted from the optical coupler 24 to the probe optical system 26 (that is, the anterior segment OCT optical system) is outputted from the fiber collimator 102. The fiber collimator 102 is configured to convert the light outputted from the anterior segment light source 12 into collimated light (parallel light). The light that became the collimated light in the fiber collimator 102 is reflected on the dichroic mirror 106, and is inputted to the two-dimensional scanner 108. The two-dimensional scanner 108 is configured to scan the inputted light in two directions, namely in x and y directions with respect to the anterior segment of the subject eye E. In the present embodiment, a Galvano scanner is used as the two-dimensional scanner 108. A scanner other than the Galvano scanner may be used as the two-dimensional scanner 108, and for example, a MEMS mirror configured capable of executing a 2-axis scan may be used. The light outputted from the two-dimensional scanner 108 is inputted to the objective lens 114 via the dichroic mirror 110 and the total reflection mirror 112. The light inputted to the objective lens 114 penetrates through the objective lens 114, is reflected on the dichroic mirror 116, and is irradiated to the anterior segment of the subject eye E (such as the cornea, the anterior chamber, and the crystalline lens). A measuring window 118 is arranged between the dichroic mirror 116 and the subject eye E. The measuring window 118 is arranged at a position that is to face the subject eye E during measurement. The measuring window 118 is arranged on a housing that is not shown, and the probe optical system 26 is housed in this housing.

The light reflected on the anterior segment of the subject eye E travels through a path that is reversed from the aforementioned path, and is inputted to the fiber collimator 102. Then, as shown in FIG. 1, it is inputted to the optical circulator 22 through the optical coupler 24. The measurement light inputted to the optical circulator 22 is inputted to an optical coupler 52 of the interference optical system 50.

As it is apparent from the foregoing description, in the anterior segment OCT optical system, an optical path L3, a part of an optical path L4 (more specifically, within a segment between the dichroic mirror 106 and the two-dimensional scanner 108), an optical path L5, an optical path L6, an optical path L8 (that is, within a segment between the total reflection mirror 112 and the dichroic mirror 116), and an optical path L12 constitute the path through which the light travels.

As described above, the light split by the optical coupler 24 of the measurement optical system 20 is inputted to the calibration optical system 30. As shown in FIG. 1, the calibration optical system 30 includes lenses 32, 35, 38, a dichroic mirror 34, a mirror 39, and a calibration mirror 36. The light inputted from the optical coupler 24 to the calibration optical system 30 is outputted from a fiber collimator that is not shown, penetrates through the lens 32 and the dichroic mirror 34, and is inputted to the calibration mirror 36 through the lens 35. The calibration light reflected by the calibration mirror 36 travels through a path that is reversed from the aforementioned path, then is inputted to the fiber collimator, and further inputted to the optical circulator 22 through the optical coupler 24. The calibration light inputted to the optical circulator 22 is inputted to the optical coupler 52 of the interference optical system 50. The lens 38 and the mirror 39 of the calibration optical system 30 are also used in the fundus OCT interferometer 1I to be described later.

The reference light that is split in the optical coupler 16 is inputted to the reference optical system 40 as described above. The reference optical system 40 comprises an optical circulator 42, lenses 44, 47, an attenuator 46, and a reference mirror 48. The reference light inputted from the anterior segment light source 12 to the reference optical system 40 is inputted to the optical circulator 42. The reference light inputted to the optical circulator 42 is emitted from a fiber collimator that is not shown and is inputted to the reference mirror 48 through the lenses 44, 47. An optical path length of the reference light outputted from the anterior segment light source 12 is adjusted by a zero-point adjusting mechanism (not shown). For the zero-point (also referred as zero-delay-line or coherence-gate) adjusting mechanism, those used in known ophthalmic apparatuses can be used, thus a detailed description thereof will be omitted. The reference light reflected by the reference mirror 48 is inputted again to the fiber collimator and then is inputted to the optical circulator 42. The reference light inputted to the optical circulator 42 is inputted to the optical coupler 52 of the interference optical system 50.

The interference optical system 50 comprises the optical coupler 52, a light receiving element 54, and a signal processor 56. In the optical coupler 52, the measurement light reflected from the subject eye E and the reference light generated by the reference optical system 40 are combined, and the combined measurement interference light is inputted to the light receiving element 54. Further, in the optical coupler 52, the calibration light generated by the calibration optical system 30 and the reference light generated by the reference optical system 40 are combined, and the combined calibration interference light is inputted to the light receiving element 54. An InGaAs-based element may be used as the light receiving element 54, for example, and interference of the measurement interference light and the calibration interference light is measured for each wavelength in the light receiving element 54. Further, an interference signal corresponding to an intensity of the measured interference light is inputted to the signal processor 56. The signal processor 56 is configured to sample the acquired interference signal. Known data collection devices (so-called DAQs) may be used as the signal processor 56. The sampled interference signal is inputted to a processor 200 to be described later. The processor 200 is configured to execute Fourier transform processing and the like on the interference signal, by which tomographic images of the anterior segment along scan lines are acquired.

Figure 3:
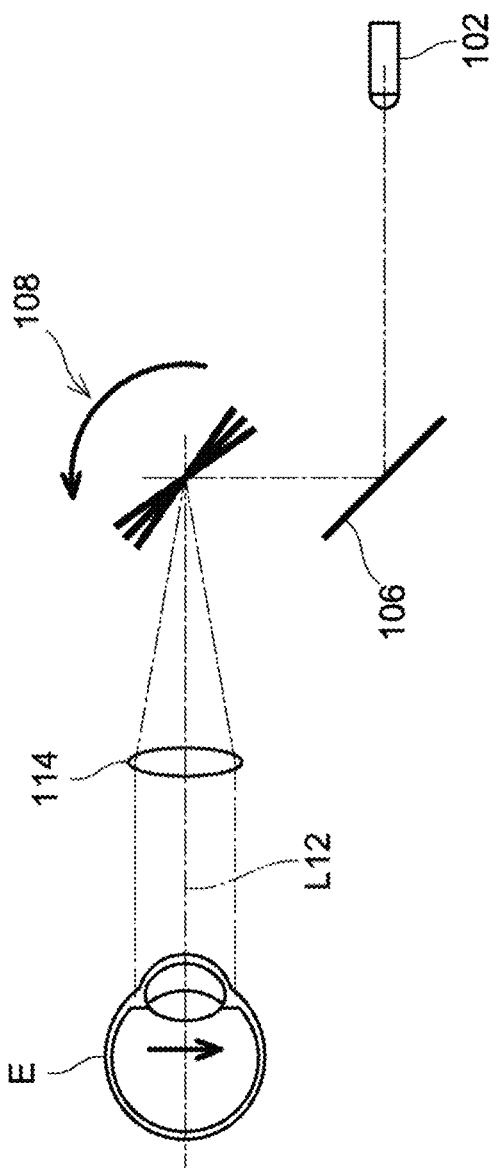
FIG. 3 schematically shows an optical path of light in the anterior segment OCT optical system.

A scan in the anterior segment OCT optical system will be described with reference to FIG. 3. FIG. 3 indicates the optical path through which the light outputted from the fiber collimator 102 is irradiated on the subject eye E, indicating only some of the optical members arranged on the optical path (that is, the dichroic mirror 106, the two-dimensional scanner 108, and the objective lens 114) with other optical members omitted from depiction. As shown in FIG. 3, in the anterior segment OCT optical system, the two-dimensional scanner 108 is arranged at a rear focal point of the objective lens 114. Due to this, rays of light scanned by the two-dimensional scanner 108 are irradiated to the subject eye E by being parallel to an optical axis (on the optical path L12). That is, a telecentric scan is performed in the anterior segment OCT optical system, thus an image with less distortion can be acquired when a tomographic image of the subject eye E is captured. Further, a fiber end surface inside the fiber collimator 102 is arranged at a conjugating position with the anterior segment of the subject eye E. Due to this, the light outputted from the fiber collimator 102 can be focused in the anterior segment of the subject eye E. As such, the tomographic image of the anterior segment of the subject eye E can suitably be captured by the anterior segment OCT optical system.

Next, the fundus OCT interferometer 11 will be described. The fundus OCT interferometer 11 is used to capture images of the fundus of the subject eye E by optical coherence tomography. The fundus OCT interferometer 11 employs the Fourier domain scheme which performs light wave interference in a Fourier space, and especially uses spectrum domain OCT (SD-OCT) which captures tomographic images of the fundus of the subject eye E by detecting spectrum information using a fixed wavelength light source that outputs light with a wide-band wavelength and a spectrometer. Shapes of respective parts of the fundus of the subject eye E (such as the retina and choroid) can be measured from the tomographic images captured by the fundus OCT interferometer 11. The fundus OCT interferometer 11 is not limited to the SD-OCT, and may use, for example, another OCT using the Fourier domain scheme (such as SS-OCT) or a scheme other than the Fourier domain scheme (such as time-domain scheme).

As shown in FIG. 1, the fundus OCT interferometer 11 comprises a fundus light source 62, a measurement optical system 66, the calibration optical system 30, a reference optical system 70, and an interference optical system 80.

The fundus light source 62 is a fixed wavelength-type light source. The fundus light source 62 is configured to output light having a central wavelength that differs from that of the light outputted from the anterior segment light source 12, and is capable of outputting light with a central wavelength of 0.40 µm or more and 1.15 µm or less, for example. Further, for example, the fundus light source 62 may be configured to output light having a half width in a wavelength range that differs from a wavelength range of a half width of the light outputted by the anterior segment light source 12. In this embodiment, the fundus light source 62 outputs light with a central wavelength of 0.83 µm. The light with the central wavelength of 0.40 µm or more and 1.15 µm or less has a high intraocular penetration rate. Due to this, by outputting the light with the central wavelength of 0.40 µm or more and 1.15 µm or less from the light source, the light can sufficiently be provided to the fundus of the subject eye E. Further, silicon-based light receiving elements have a high sensitivity to light with the central wavelength of 0.40 µm or more and 0.95 µm or less. Further, light with the central wavelength of 0.95 µm or more and 1.15 µm or less is not dispersed much by water, thus fundus OCT images with high quality can be acquired by irradiating the subject eye E with light in that range. Thus, by outputting the light with the central wavelength of 0.40 µm or more and 1.15 µm or less from the light source, the tomographic images of the fundus of the subject eye E can suitably be captured.

An optical coupler 64 is connected to the fundus light source 62. As such, light outputted from the fundus light source 62 is inputted to the optical coupler 64 and is split in the optical coupler 64 into measurement light and reference light, for example, at a ratio of 9:1, and these lights are respectively inputted to the measurement optical system 66 and the reference optical system 70.

The measurement optical system 66 comprises an optical coupler 68 and the probe optical system 26. The measurement light inputted from the fundus light source 62 to the measurement optical system 66 is inputted to the optical coupler 68 and is split in the optical coupler 68, for example, at a ratio of 99:1, and these lights are inputted respectively to the probe optical system 26 and the calibration optical system 30.

Figure 4:
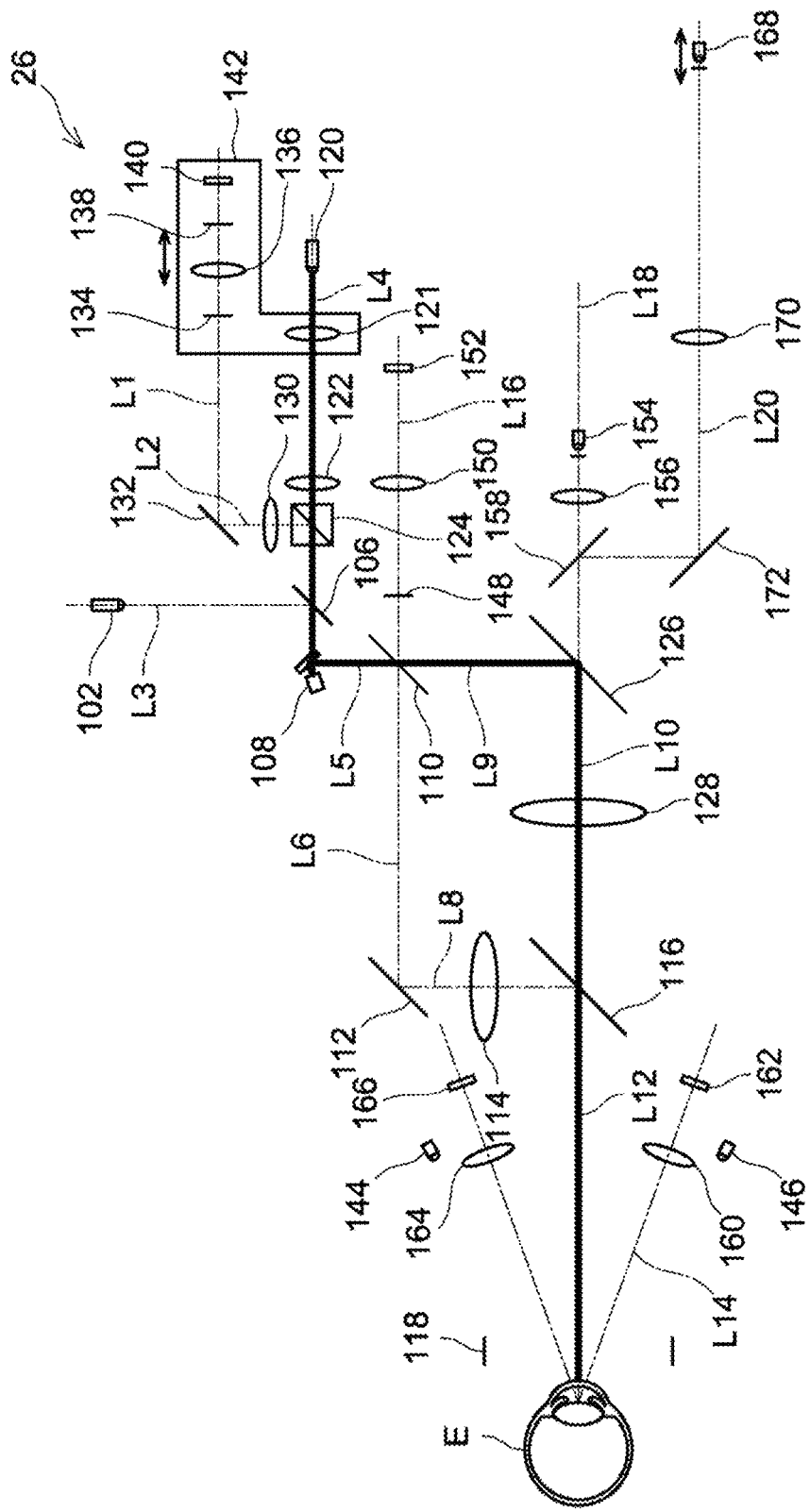
FIG. 4 is a diagram for explaining a fundus OCT optical system of the ophthalmic device of the embodiment.

As shown in FIG. 4, the fundus OCT optical system is constituted of a fiber collimator 120, a lens 121, a lens 122, a polarization beam splitter 124, the dichroic mirror 106, the two-dimensional scanner 108, the dichroic mirror 110, a dichroic mirror 126, an objective lens 128, and the dichroic mirror 116. The dichroic mirror 126 is configured to allow light with wavelengths longer than 0.90 µm to penetrate and reflect light with wavelengths shorter than 0.90 µm.

Light inputted from the optical coupler 68 to the probe optical system 26 (that is, the fundus OCT optical system) is outputted from the fiber collimator 120, penetrates through the lens 121, the lens 122, the polarization beam splitter 124, and the dichroic mirror 106, and is inputted to the two-dimensional scanner 108. The two-dimensional scanner 108 scans the inputted light in two directions, namely in the x and y directions with respect to the fundus of the subject eye E. The light outputted from the two-dimensional scanner 108 penetrates through the dichroic mirror 110, is reflected on the dichroic mirror 126, and enters the objective lens 128. The light that entered the objective lens 128 penetrates through the objective lens 128 and through the dichroic mirror 116, and is irradiated to the fundus of the subject eye E (such as the retina and choroid).

The measurement light reflected by the fundus of the subject eye E travels through a path that is reversed from the aforementioned path, then is inputted to the fiber collimator 120. Then, as shown in FIG. 1, it is inputted again to the optical coupler 64 via the optical coupler 68. The measurement light inputted to the optical coupler 64 is inputted to the interference optical system 80.

As it is apparent from the foregoing description, in the fundus OCT optical system, the optical path L4, the optical path L5, an optical path L9, an optical path L10, and the optical path L12 constitute the path through which the light travels. As such, a part of the optical path L4 (more specifically, the segment between the dichroic mirror 106 and the two-dimensional scanner 108), the optical path L5, and the optical path L12 constitute a path overlapping between the anterior segment OCT optical system and the fundus OCT optical system, while the optical paths L8, L6, and L3 constitute a path dedicated to the light of the anterior segment OCT optical system and a remaining segment of the optical path L4, the optical path L9, and the optical path L10 constitute a path dedicated to the light of the fundus OCT optical system.

As described above, the light split in the optical coupler 68 of the measurement optical system 66 is inputted to the calibration optical system 30. As shown in FIG. 1, the light inputted to the calibration optical system 30 is outputted from a fiber collimator that is not shown, reflected on the dichroic mirror 34 through the lens 38 and the mirror 39, and is inputted to the calibration mirror 36 through the lens 35. The calibration light reflected by the calibration mirror 36 is inputted to the fiber collimator again through the lens 35, the dichroic mirror 34, the mirror 39, and the lens 38, and is inputted to the interference optical system 80 through the optical couplers 68, 64.

On the other hand, the reference light split in the optical coupler 64 is inputted to the reference optical system 70 as described above. The reference optical system 70 is provided with lenses 72, 74 and a reference mirror 76. The reference light inputted from the fundus light source 62 to the reference optical system 70 is emitted from a fiber collimator that is not shown, and is inputted to the reference mirror 76 through the lenses 72, 74. An optical path length of the reference light outputted from the fundus light source 62 is adjusted by a zero-point adjusting mechanism (not shown). The reference light reflected on the reference mirror 76 is inputted again to the fiber collimator and is inputted to the interference optical system 80 through the optical coupler 64.

The interference optical system 80 comprises lenses 82, 88, a diffraction grating 84, a prism 86, and a light receiving element 89. The measurement light reflected on the subject eye E and the reference light generated by the reference optical system 70 are combined in the interference optical system 80, and the combined measurement interference light is inputted to the light receiving element 89. Further, the calibration light generated by the calibration optical system 30 and the reference light generated by the reference optical system 70 are combined, and the combined calibration interference light is inputted to the light receiving element 89. Specifically, the measurement interference light and the calibration interference light are emitted from a fiber collimator that is not shown, and pass through the lens 82 and the diffraction grating 84. Due to this, each of the interference light is separated into wavelength spectrums. Then, each of the separated light is inputted to the prism 86, by which it is converted from spectrum data that is linear to wavelengths into spectrum data linear to the wave numbers (wavenumber spectrum). Then, each of the light that has been converted into wavenumber spectrum in the prism 86 is inputted to the light receiving element 89 through the lens 88. A line sensor (such as a CCD camera) may be used as the light receiving element, for example. In the light receiving element 89, interference of the measurement interference light and the calibration interference light is measured for each wave number. Then, an interference signal corresponding to an intensity of the measured interference light is inputted to the processor 200 to be described later. The processor 200 is configured to execute Fourier transform processing and the like on the interference signal, by which tomographic images of the fundus along scan lines are acquired.

Figure 5:
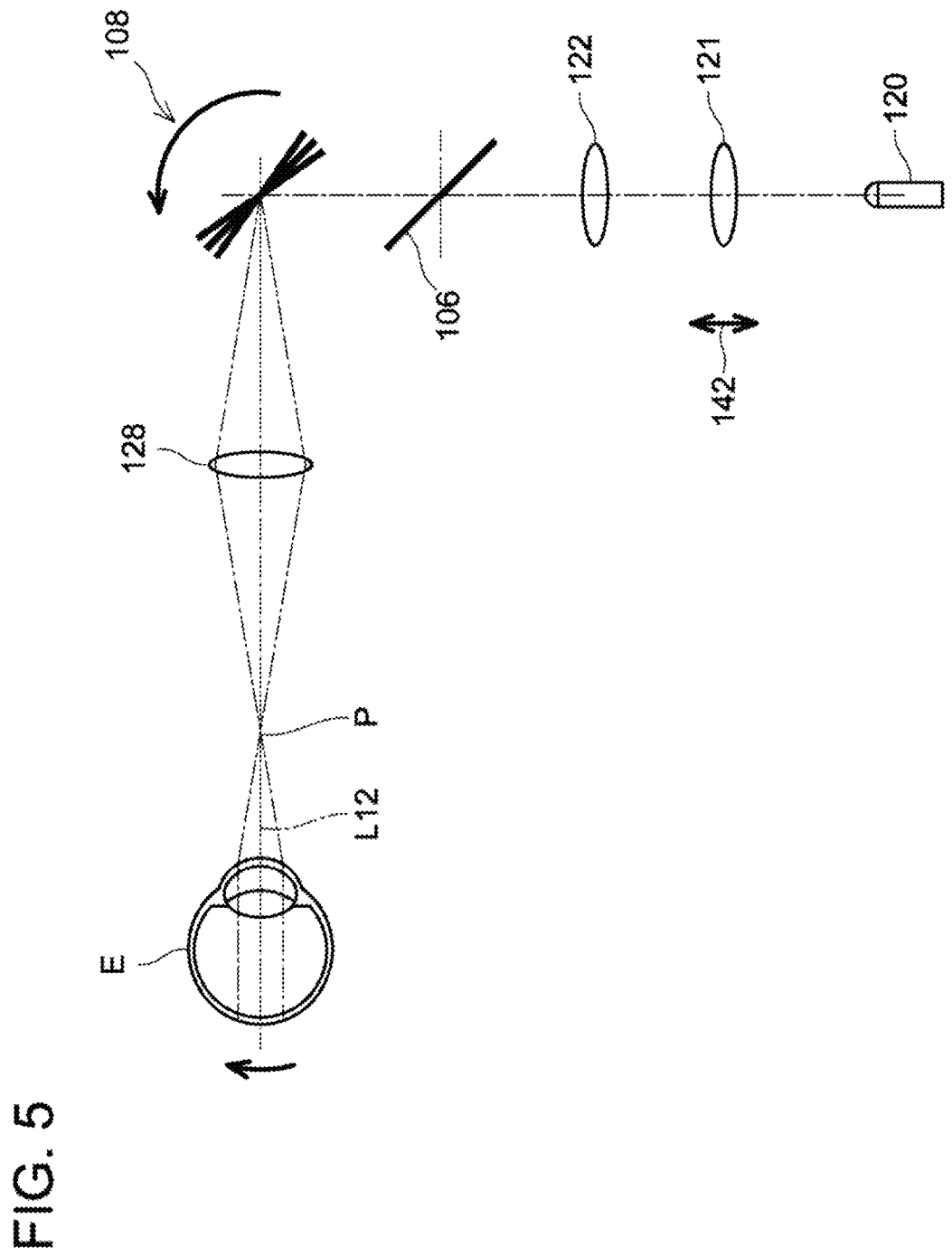
FIG. 5 schematically shows an optical path of light in the fundus OCT optical system.

A scan in the fundus OCT optical system will be described with reference to FIG. 5. FIG. 5 indicates the optical path through which the light outputted from the fiber collimator 120 is irradiated on the subject eye E, indicating only some of the optical members arranged on the optical path (that is, the lens 121, the lens 122, the dichroic mirror 106, the two-dimensional scanner 108, and the objective lens 128) with other optical members omitted from depiction. Further, the two-dimensional scanner 108 is disposed at a position conjugate with a position P between the subject eye E and the objective lens 128. Due to this, in the fundus OCT optical system, light scanned by the two-dimensional scanner 108 intersects with the optical axis of the ophthalmic device 1 (optical path L12) in a segment between the objective lens 128 and the subject eye E. That is, in the fundus OCT optical system, the scan forms a pivot point in front of the subject eye E. Further, in the fundus OCT optical system, the position P of the pivot point is set such that the rays of light intersecting between the objective lens 128 and the subject eye E are collimated to be parallel to the optical axis of the ophthalmic device 1 when they enter into the subject eye E. That is, in the fundus OCT optical system, when the subject eye E is regarded as one lens, the position P of the pivot point is set to match a rear focal point of this lens. Due to this, in the fundus OCT optical system, the rays of the light scanned by the two-dimensional scanner 108 reach the fundus by being parallel to the optical axis of the ophthalmic device 1. That is, a telecentric scan is performed in the fundus OCT optical system, and thus an image with less distortion can be acquired when a tomographic image of the subject eye E is captured. A position of the pivot point is not particularly limited, however, it may for example be set to a position 5 to 25 mm in front of the cornea of the subject eye E. Further, for example, when the position of the pivot point is to be set with respect to a general refractivity (about 60D) and focal distance (about 17 mm) of the subject eye E, the position of the pivot point may be set to about 15 mm in front of the cornea of the subject eye E based on a position of a principal point on the cornea side being about 2 mm in front of a corneal apex.

Further, an end surface of the fiber collimator 120 is disposed at a position conjugate with the fundus of the subject eye E. Due to this, the light emitted from the fiber collimator 120 can be concentrated at the fundus of the subject eye E. A position of the lens 121 can be changed by actuating a focal point adjusting mechanism 142 to be described later. Due to this, the light emitted from the fiber collimator 120 can be concentrated at the fundus of the subject eye E according to the refractivity of the subject eye E. Thus, tomographic images of the fundus of the subject eye E can suitably be captured by the fundus OCT optical system.

Figure 6:
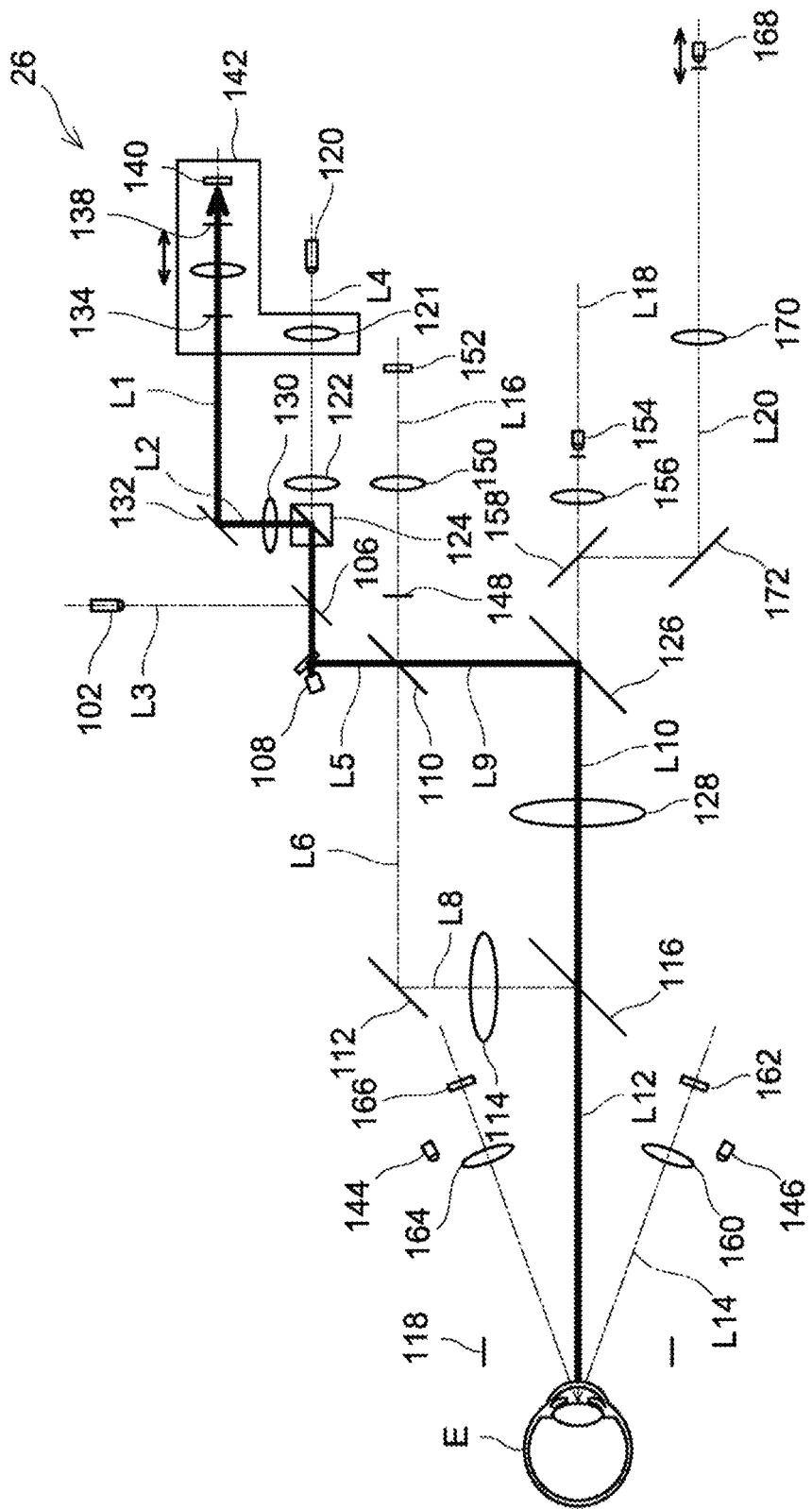
FIG. 6 is a diagram for explaining a light receiving system for receiving light reflected on a subject eye in a refractometric measurement optical system.

Next, the refractometric measurement optical system will be described. The refractometric measurement optical system is an optical system used for measuring the refractivity of the subject eye E. A light floodlighting system of the refractometric measurement optical system that emits light to the subject eye E has a same configuration as the light floodlighting system of the fundus OCT optical system. Due to this, a light receiving system of the refractometric measurement optical system will be described. As shown in FIG. 6, the light receiving system of the refractometric measurement optical system is constituted of the dichroic mirror 116, the objective lens 128, the dichroic mirror 126, the dichroic mirror 110, the two-dimensional scanner 108, the dichroic mirror 106, the polarization beam splitter 124, a lens 130, a mirror 132, an aperture 134, a lens 136, a donut lens 138, a two-dimensional sensor 140, a focal point adjusting mechanism 142, and a fogging mechanism (not shown).

In the light receiving system of the refractometric measurement optical system, reflected light from the subject eye E is irradiated to the polarization beam splitter 124 via the dichroic mirror 116, the objective lens 128, the dichroic mirror 126, the dichroic mirror 110, the two-dimensional scanner 108, and the dichroic mirror 106. In the polarization beam splitter 124, only an S-polarization component in the light scattered on the fundus of the subject eye E is reflected and is irradiated to the mirror 132 through the lens 130. The light irradiated on the mirror 132 penetrates the aperture 134, the lens 136, and the donut lens 138, and forms a ring-shaped image on a light receiving plane of the two-dimensional sensor 140. The refractivity of the subject eye E is calculated based on the ring image formed in the two-dimensional sensor 140. In this embodiment, the light scattered on the fundus of the subject eye E is formed as the ring image on the light receiving plane of the two-dimensional sensor 140 by using the donut lens 138, however, without being limited to such an example, a lens array may be used instead of the donut lens 138 to form a dot-pattern image on the light receiving plane of the two-dimensional sensor 140. The image detected (captured) by the two-dimensional sensor 140 is inputted to a processor.

Further, the refractometric measurement optical system comprises the focal point adjusting mechanism 142. The focal point adjusting mechanism 142 comprises a driving device (not shown) configured to integrally move the lens 121, the aperture 134, the lens 136, the donut lens 138, and the two-dimensional sensor 140 in the direction of the optical axis (optical paths L1, L4). The focal point adjusting mechanism 142 is configured to drive the driving device to move the position of the fiber end surface in the fiber collimator 120 and the position of the two-dimensional sensor 140 to positions that are conjugate with the fundus of the subject eye E in accordance with the refractivity of the subject eye E, thus refractometric measurement can be performed with high accuracy.

Further, the refractometric measurement optical system comprises the two-dimensional scanner 108. The two-dimensional scanner 108 is configured to scan measurement rays in a circular pattern about the optical axis on the pupil of the subject eye E. By doing so, measurement can be performed while avoiding an opaque site caused by cataract or the like, and also speckle noise generated by use of light source with high coherence can be suppressed. Further, a part of the refractometric measurement optical system has the same configuration as the fundus OCT optical system, thus the measurement rays are scanned in the circular pattern while maintaining their position separated from the measurement optical axis by a predetermined distance within the subject eye E and reach the fundus. Due to this, since the refractivity of the subject eye E can be measured based on the reflected light from the fundus at a substantially constant position regardless of the axial length of the subject eye E, the refractometric measurement can be performed with high accuracy.

Figure 7:
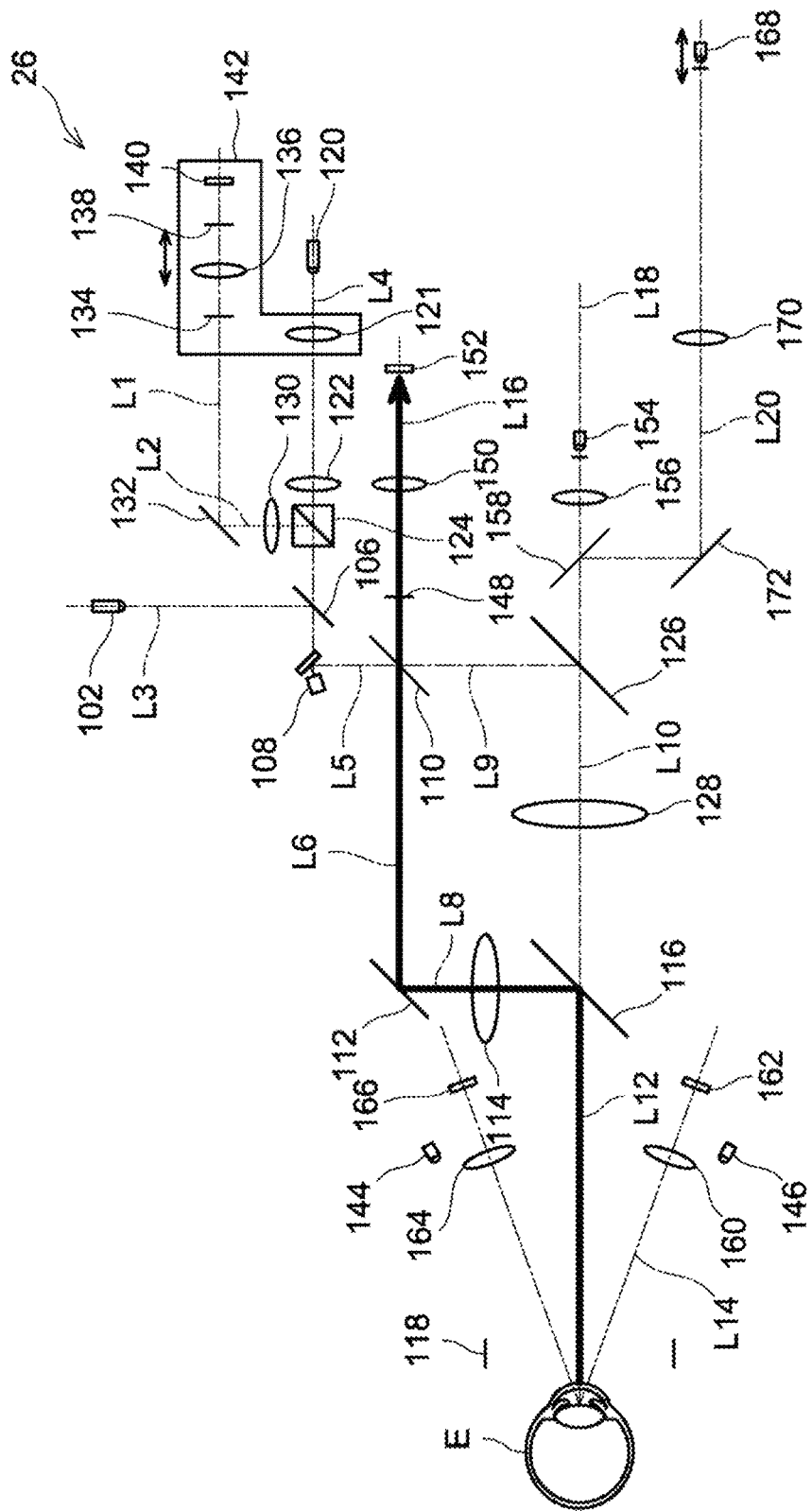
FIG. 7 is a diagram for explaining a front monitoring optical system of the ophthalmic device of the embodiment.

Next, the front monitoring optical system will be described. As shown in FIG. 7, the front monitoring optical system is constituted of LEDs 144, 146, the dichroic mirror 116, the objective lens 114, the total reflection mirror 112, the dichroic mirror 110, an aperture 148, a lens 150, and a two-dimensional sensor 152.

The LEDs 144, 146 are arranged on obliquely front sides of the subject eye E and are configured to illuminate the anterior segment of the subject eye E. The LEDs 144, 146 are configured to irradiate light with the central wavelength of 0.76 μm to the subject eye E. The light reflected on the subject eye E is reflected on the dichroic mirror 116, penetrates through the objective lens 114, is reflected on the total reflection mirror 112, penetrates the dichroic mirror 110, the aperture 148, and the lens 150, and forms a front image of the anterior segment on the two-dimensional sensor 152. The image of the anterior segment of the subject eye E captured by the two-dimensional sensor 152 is displayed on a display device that is not shown. The aperture 148 is arranged at the rear focal point of the objective lens 114, and is configured such that its image magnification does not change even when the anterior segment image is defocused.

Figure 8:
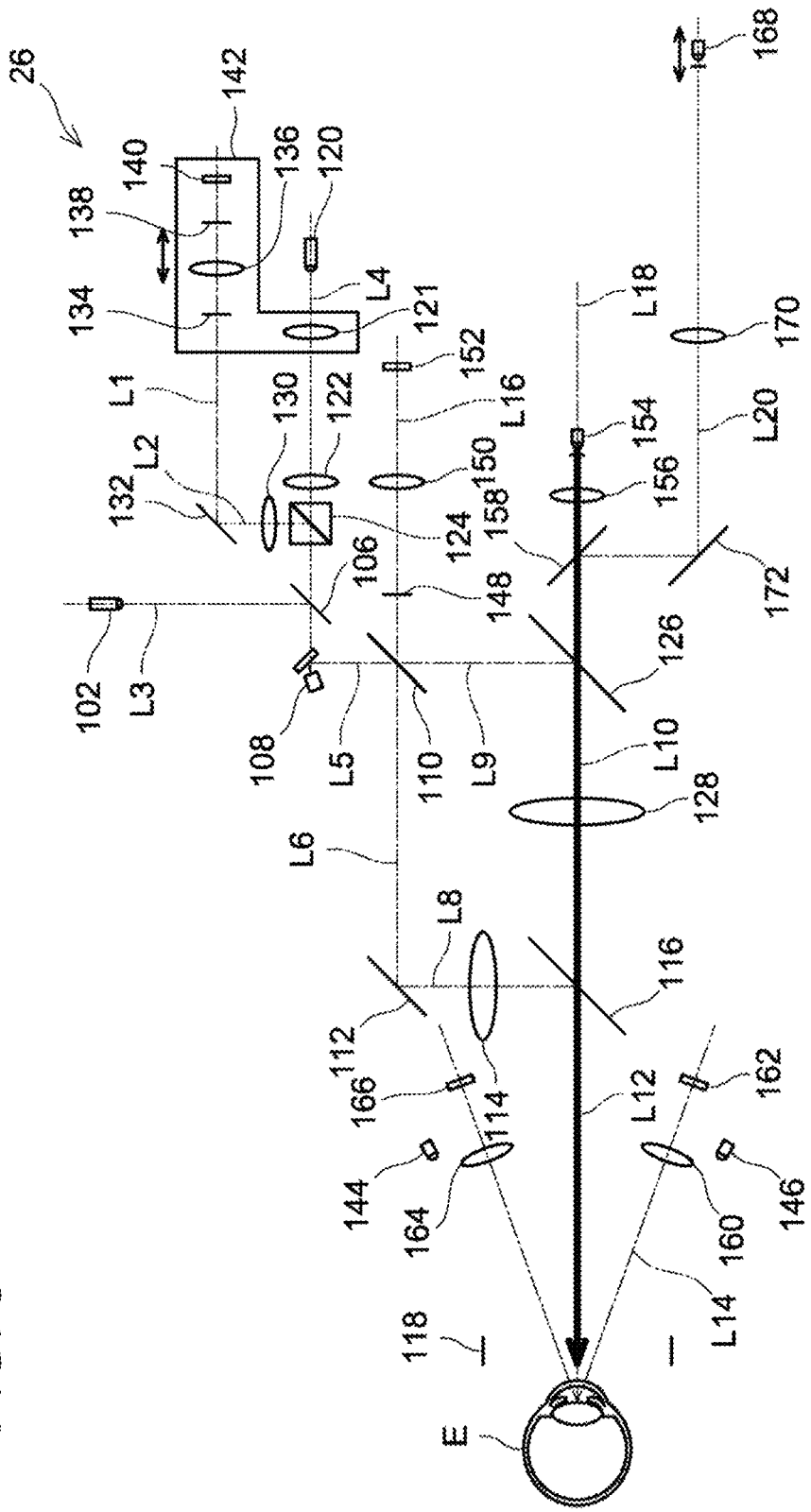
FIG. 8 is a diagram for explaining a position detection light floodlighting optical system of the ophthalmic device of the embodiment.

Next, the position detection light floodlighting optical system will be described. As shown in FIG. 8, the position detection light floodlighting optical system is constituted of a LED 154, a lens 156, a dichroic mirror 158, the dichroic mirror 126, the objective lens 128, and the dichroic mirror 116. The LED 154 is configured to output light with the central wavelength of 0.94 μm. The light outputted from the LED 154 penetrates through the lens 156, the dichroic mirrors 158, 126, the objective lens 128, and the dichroic mirror 116, and is irradiated to a cornea of the subject eye E. The light irradiated to the subject eye E is mirror-reflected on a surface of the cornea of the subject eye E, and a virtual image of a light emitting surface of the LED 154 is formed on an extended line of the corneal apex.

Figure 9:
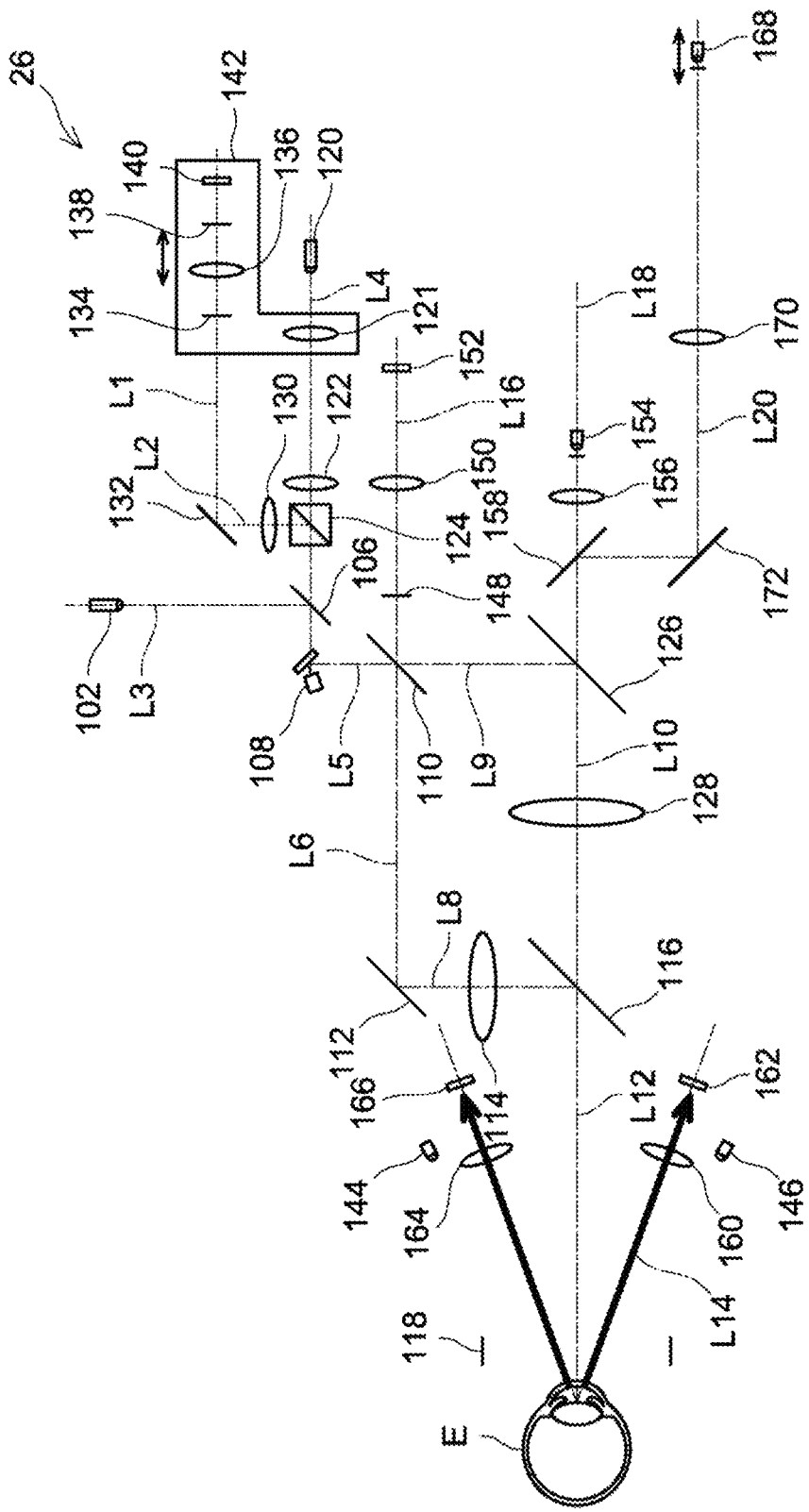
FIG. 9 is a diagram for explaining a position detection light receiving optical system of the ophthalmic device of the embodiment.

Next, the position detection light receiving optical system will be described. The position detection light receiving optical system is configured to detect a corneal apex position in a direction (i.e., lateral direction) perpendicularly intersecting the optical axis (optical path L12) and detect a corneal apex position in the optical axis direction (i.e., depth direction). As shown in FIG. 9, the position detection light receiving optical system is constituted of a lens 160, a two-dimensional sensor 162, a lens 164, and a two-dimensional sensor 166. The lens 160 and the two-dimensional sensor 162 are arranged on one of the obliquely front sides of the subject eye E. The lens 164 and the two-dimensional sensor 166 are also arranged on the other of the obliquely front sides of the subject eye E. The lens 164 and the two-dimensional sensor 166 are arranged at positions symmetric to the lens 160 and the two-dimensional sensor 162 with respect to the optical axis (optical path L12). Light reflected at a position that is slightly offset from the corneal apex of the subject eye E is reflected in an oblique direction, penetrates the lens 160, and a virtual image of the light emitting surface of the LED 154 is projected on the two-dimensional sensor 162. Similarly, the light reflected at a position that is slightly offset from the corneal apex of the subject eye E penetrates the lens 164, and a virtual image of the light emitting surface of the LED 154 is projected on the two-dimensional sensor 166. In the ophthalmic device of the present embodiment, the corneal apex position in the direction (i.e., lateral direction) perpendicularly intersecting the optical axis (optical path L12) and the corneal apex position in the optical axis direction (i.e., depth direction) are detected based on the virtual images of the light emitting surface of the LED 154 detected by the two-dimensional sensors 162, 166.

After the position of the corneal apex of the subject eye E is detected based on detection results of the two-dimensional sensor 162 and the two-dimensional sensor 166, the housing that houses the probe optical system 26 is driven by a driver device that is not shown, and the housing is positioned at a measurement position relative to the corneal apex of the subject eye E. Due to this, the measuring window 118 is positioned relative to the subject eye E, and the objective lenses 114, 128 of the probe optical system 26 are thereby positioned. When the measuring window 118 (objective lenses 114, 128 of the probe optical system 26) is positioned relative to the subject eye E, positions of the measuring window 118 and the objective lenses 114, 128 relative to the subject eye E do not change while acquiring the tomographic images of the anterior segment and the fundus of the subject eye E and the refractivity thereof.

Figure 10:
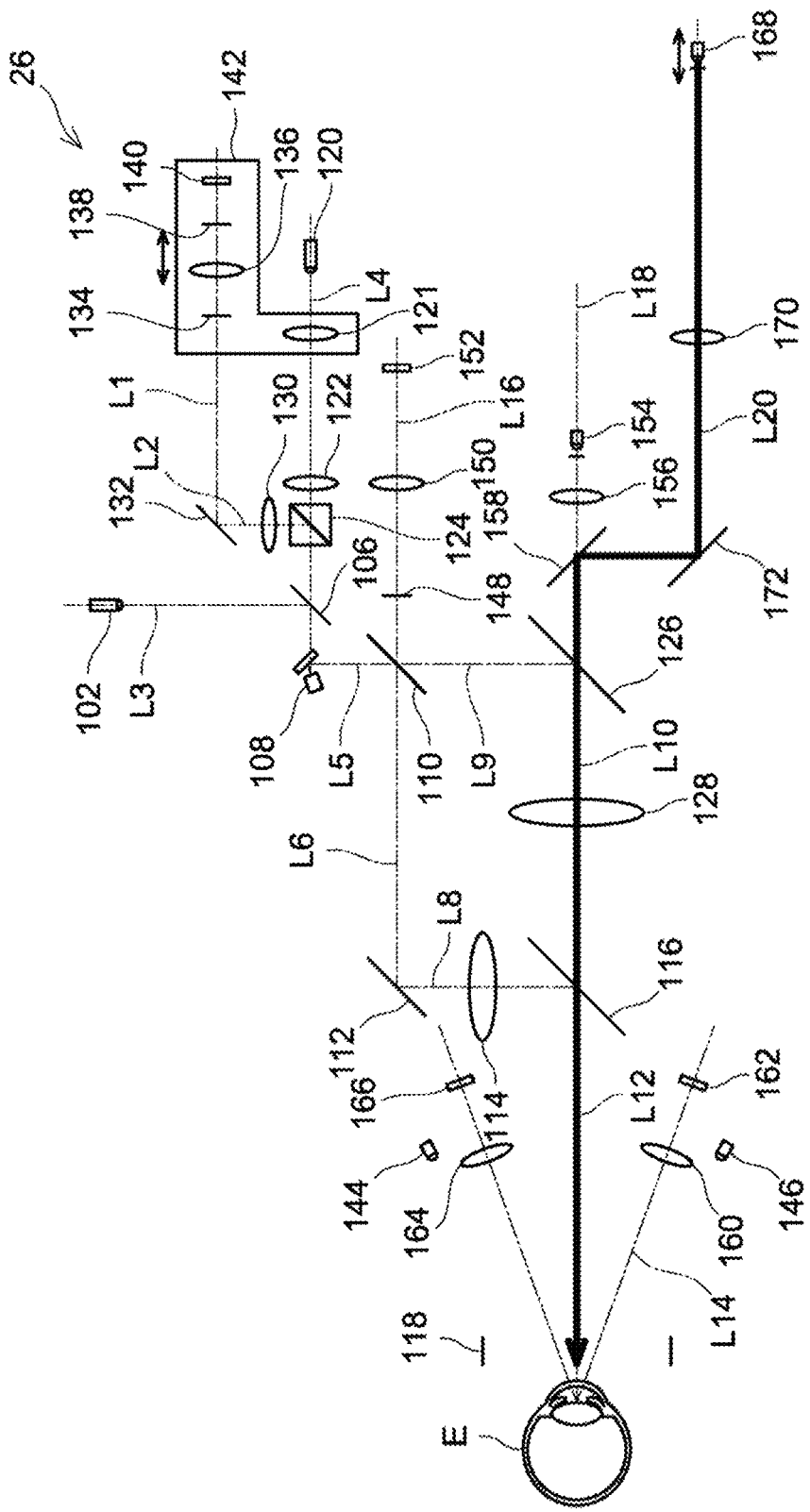
FIG. 10 is a diagram for explaining a gaze fixing target optical system of the ophthalmic device of the embodiment.

Next, the gaze fixing target optical system will be described. As shown in FIG. 10, the gaze fixing target optical system is constituted of a LED 168, a lens 170, a mirror 172, the dichroic mirrors 158, 126, the objective lens 128, and the dichroic mirror 116. The LED 168 is configured to output white light. The light from the LED 168 penetrates an image film on which a symbol for fixing vision of an examined person is printed, and is reflected on the mirror 172. The light reflected on the mirror 172 is further reflected on the dichroic mirror 158, penetrates through the dichroic mirror 126, the objective lens 128, and the dichroic mirror 116, and is irradiated toward the subject eye E. The LED 168 and the image film are configured movable in an optical axis direction (i.e., direction along an optical path L20), thus positions of the LED 168 and the image film are configured to be adjusted in accordance with the refractivity of the subject eye E.

As described above, the ophthalmic device 1 of the embodiment has the two-dimensional scanner 108 arranged on the overlapping optical path where the optical path of the anterior segment OCT optical system overlaps the optical path of the fundus OCT optical system. That is, the scan in the anterior segment OCT optical system and the scan in the fundus OCT optical system are both performed by the two-dimensional scanner 108. Due to this, the internal configuration of the ophthalmic device 1 is suppressed from becoming complicated, and the number of components can be reduced. Further, as compared to a case of arranging separate scanners for scanning the light outputted from the anterior segment light source 12 and the light outputted from the fundus light source 62, synchronization of the scanners is not necessary upon measuring the subject eye E, and scanner control can thereby be facilitated.

Figure 11:
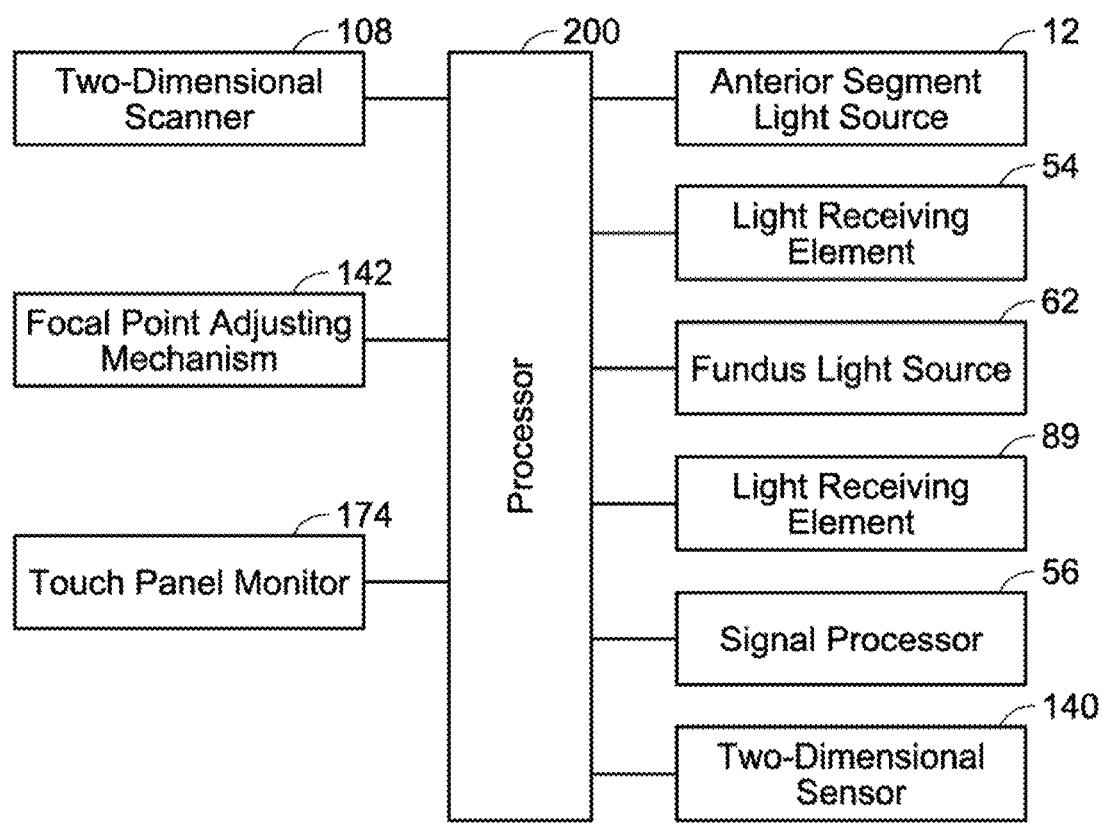
FIG. 11 shows a configuration of a control system of the ophthalmic device of the embodiment.

Next, the configuration of a control system of the ophthalmic device 1 of the embodiment will be described with reference to FIG. 11. As shown in FIG. 11, the ophthalmic device 1 is controlled by the processor 200. The processor 200 is constituted of a computer including a CPU, a ROM, and a RAM and the like. The processor 200 has the anterior segment light source 12, the light receiving element 54, and the signal processor 56 in the anterior segment OCT interferometer 10, the fundus light source 62, the light receiving element 89 in the fundus OCT interferometer 11, the two-dimensional scanner 108, the two-dimensional sensor 140, the focal point adjusting mechanism 142, and a touch panel monitor 174 connected thereto.

The processor 200 controls on/off of the anterior segment light source 12 and drives the two-dimensional scanner 108 to scan the light irradiated to the anterior segment of the subject eye E. Further, interference signals sampled by the signal processor 56 are inputted to the processor 200. The processor 200 performs Fourier transformation on the interference signals to generate tomographic images, specifies positions of respective parts in the anterior segment of the subject eye E (such as the cornea, the anterior chamber, and the crystalline lens), and calculates shapes of respective tissues in the anterior segment.

Similarly, the processor 200 controls on/off of the fundus light source 62 and drives the two-dimensional scanner 108 to scan the light irradiated to the fundus of the subject eye E. Further, interference signals corresponding to intensity of interference light detected by the light receiving element 89 are inputted to the processor 200. The processor 200 performs Fourier transformation on the interference signals from the light receiving element 89 to generate tomographic images, specifies positions of respective parts in the fundus of the subject eye E (such as the retina, and the choroid), and calculates shapes of respective tissues in the fundus.

Further, electric signals (captured image) detected by the two-dimensional sensor 140 are inputted to the processor 200, and the processor 200 calculates the refractivity of the subject eye E based on the inputted image. The data inputted to the processor 200 and the calculation result(s) are stored in a memory (not shown). The processor 200 calculates the shapes of the anterior segment and the fundus by correcting the generated tomographic images of the anterior segment and the fundus. Then, the processor 200 calculates the axial length of the subject eye E based on the calculated shapes. Correction of the tomographic images and calculation of the eye axial length will be described later.

Further, the processor 200 controls the touch panel monitor 174. The touch panel monitor 174 serves as a display providing various types of information related to the measurement result of the subject eye E to an examiner and also as an input unit for accepting instruction from the examiner. For example, the touch panel monitor 174 can display the tomographic images of the anterior segment and the fundus of the subject eye E generated by the processor 200, the corrected tomographic images of the anterior segment and the fundus, the calculated refractivity, and data acquired by other scans. Further, for example, the touch panel monitor 174 can input various settings of the ophthalmic device 1. The ophthalmic device 1 of the embodiment includes the touch panel monitor 174, however, it may be any configuration capable of displaying and inputting information as aforementioned, and may be a monitor and an input device (such as a keyboard and a mouse).

In this embodiment, the processor 200 simultaneously performs the above-mentioned light irradiation to the anterior segment of the subject eye E by the anterior segment light source 12 and the above-mentioned light irradiation to the fundus of the subject eye E by the fundus light source 62. That is, the processor 200 acquires the interference signals obtained from the anterior segment and the interference signals obtained from the fundus by driving the two-dimensional scanner 108 in a state where the light from the anterior segment light source 12 and the light from the fundus light source 62 are both inputted to the two-dimensional scanner 108. Due to this, in the present embodiment, the anterior segment and the fundus of the subject eye E can be measured with the subject eye E in a substantially identical state during those measurements. Hereinbelow, processes for measuring the anterior segment, the fundus, and the refractivity of the subject eye E, correcting the tomographic images of the anterior segment and the fundus, and measuring the axial length will be described with reference to FIGS. 12 to 23.

Figure 12:
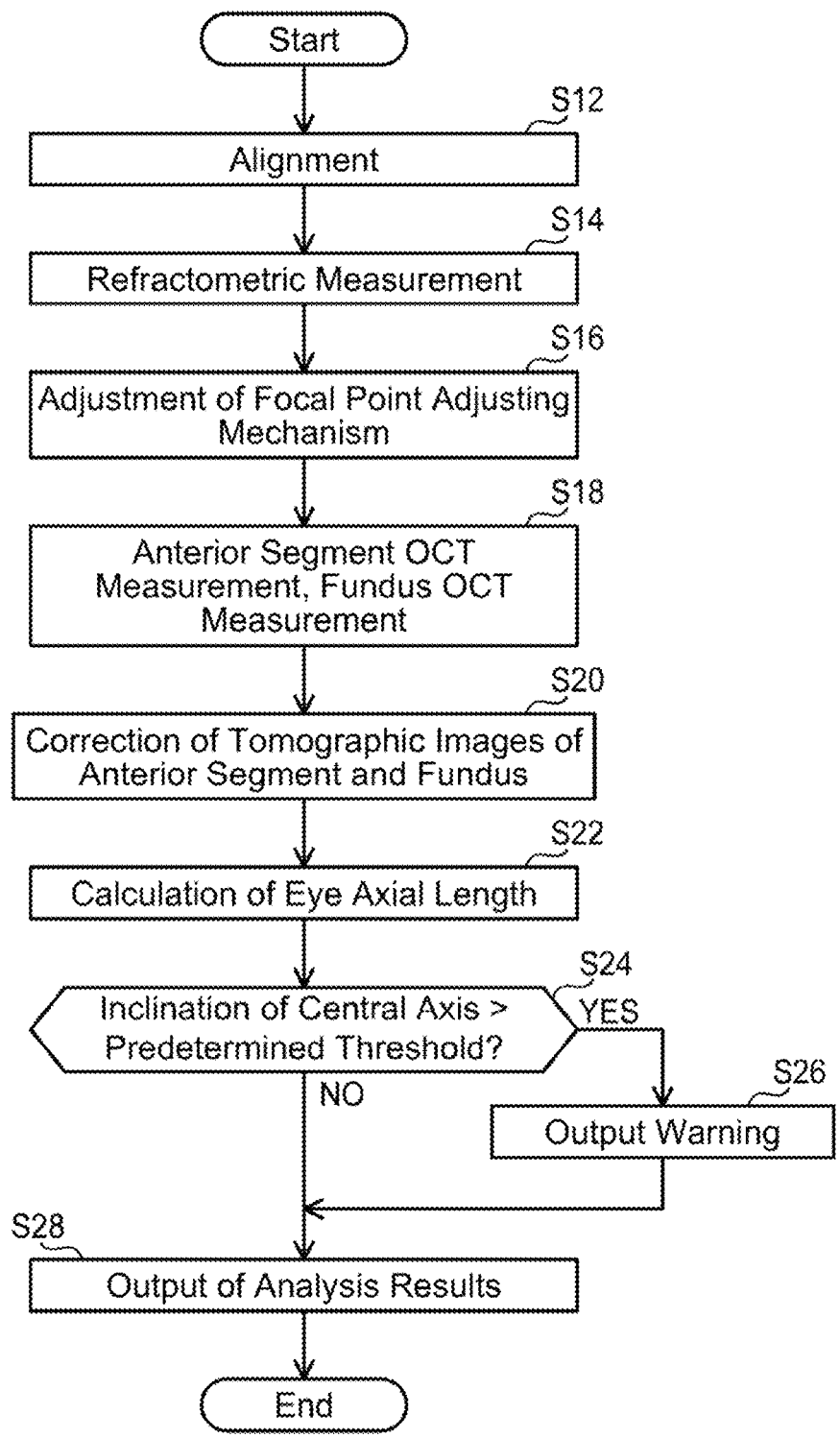
FIG. 12 is a flowchart showing processes for inspecting a subject eye using the ophthalmic device of the embodiment.

FIG. 12 is a flowchart showing an example of processes for executing various measurements on the subject eye E using the ophthalmic device 1. As shown in FIG. 12, firstly, when the examiner inputs an instruction to start the examination to the touch panel monitor 174, the processor 200 performs alignment of the subject eye E and the ophthalmic device 1 (S12). The alignment is performed using the alignment optical system (not shown) included in the ophthalmic device 1. A method used in a known ophthalmic device can be employed in the alignment using the alignment optical system, thus detailed descriptions thereof will be omitted.

When the alignment of the subject eye F and the ophthalmic device 1 is completed, the processor 200 performs the refractometric measurement (S14). The refractometric measurement is performed in the following procedure. Firstly, the processor 200 adjusts the two-dimensional scanner 108. At this occasion, the processor 200 adjusts a circle diameter to be scanned and an irradiation position on the subject eye E based on a preset value (initial setting value). The initial setting value can be set, for example based on a pupil diameter of the subject eye E, to a value that is smaller than the pupil diameter. Further, if the subject has taken the examination before, the two-dimensional scanner 108 may be adjusted based on the measurement results from the previous examination.

After the adjustment of the two-dimensional scanner 108 has been completed, the processor 200 measures the refractivity by turning on the fundus light source 62 to read the images detected by the two-dimensional sensor 140 and analyzing the images. At this occasion, the refractivity may be measured in a state of having excluded refractive adjustment power of the crystalline lens of the subject eye E by using the fogging mechanism that is not shown. A configuration used in a known ophthalmic device can be employed as the fogging mechanism, thus detailed description thereof will be omitted.

When the refractometric measurement is completed, the processor 200 adjusts the focal point adjusting mechanism 142 based on the result of the refractometric measurement of S14 (S16). For example, when the subject eye E is hypermetropic or myopic, the processor 200 drives the focal point adjusting mechanism 142 to move the positions of a focal point (beam waist) of the fundus light source 62 and the two-dimensional sensor 140 relative to the subject eye E, and the two-dimensional sensor 140 is moved to a position conjugate with the fundus of the subject eye E.

Figure 13:
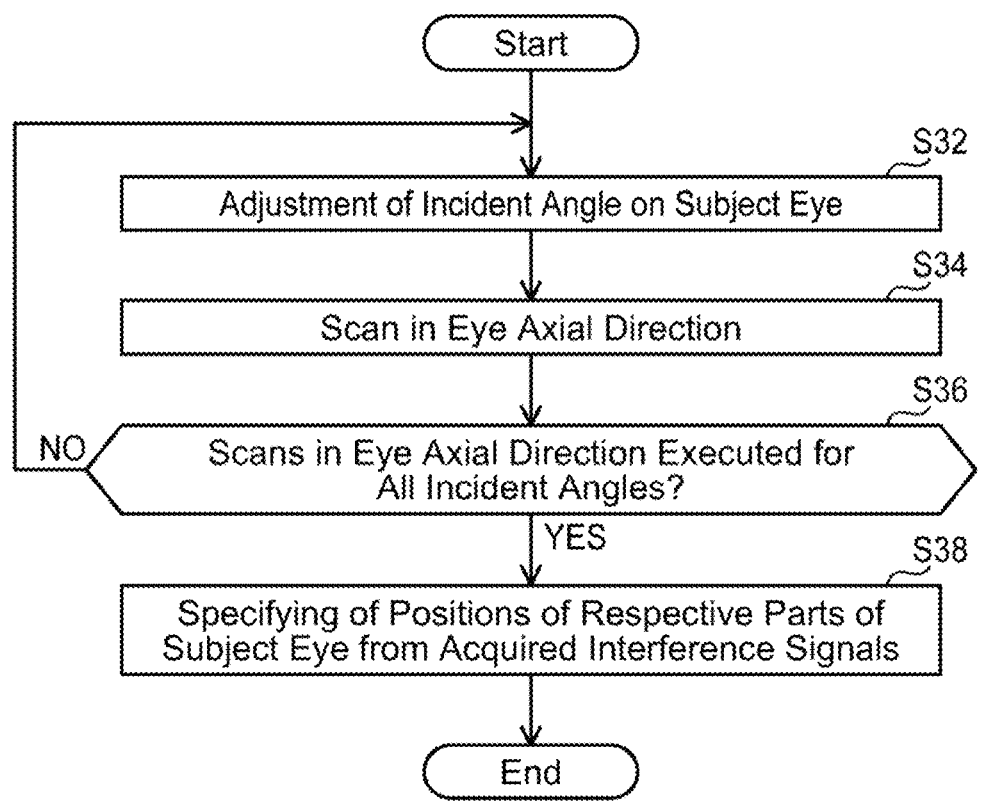
FIG. 13 is a flowchart showing processes of OCT measurement.

Next, the processor 200 simultaneously performs the anterior segment OCT measurement and the fundus OCT measurement (S18). Firstly, the anterior segment OCT measurement will be described with reference to FIG. 13. As shown in FIG. 13, the processor 200 sets the two-dimensional scanner 108 to one of scan angles that are preset radially about the corneal apex of the subject eye E (S32). That is, the processor 200 sets the two-dimensional scanner 108 so that the light outputted from the anterior segment light source 12 is scanned radially along one of the plurality of preset angular positions arranged along a circumferential direction about the corneal apex of the subject eye E. Due to this, the light outputted from the anterior segment light source 12 is inputted to the subject eye E at an incident position corresponding to the set scan angle. Here, the two-dimensional scanner 108 is set such that the light outputted from the anterior segment light source 12 in each of B-scans that are scanned radially passes through the corneal apex. In the description herein, the process of changing the incident position of the light from the light source by changing the scan angle of the two-dimensional scanner 108 will be termed "B-scan".

Figure 14:
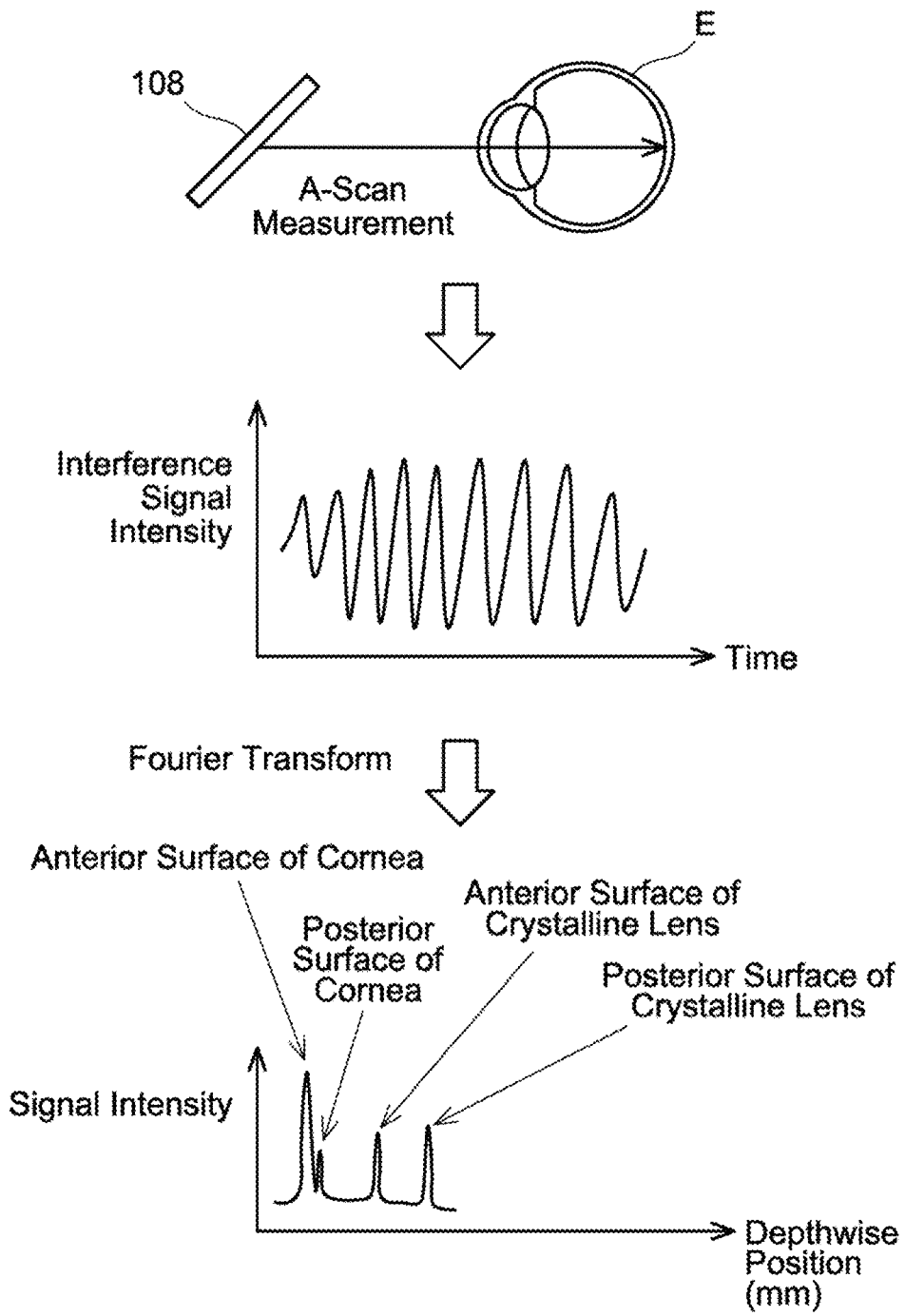
FIG. 14 is a diagram for explaining a procedure for processing an interference signal waveform obtained by the anterior segment OCT interferometer.

When the setting on the two-dimensional scanner 108 is completed, the processor 200 turns on the anterior segment light source 12 and intakes the interference signals sampled by the signal processor 56 while changing frequency of the light irradiated from the anterior segment light source 12 (S34). The interference signals sampled by the signal processor 56 are processed as a signal of which signal intensity changes over time as shown in FIG. 14, and this signal is a signal constituted of interference waves that combined the reflected light that is reflected from each part of the subject eye E (such as anterior and posterior surfaces of the cornea and anterior and posterior surfaces of the crystalline lens) and the reference light. Thus, by subjecting the signals inputted from the signal processor 56 to Fourier transform, the processor 200 can specify depthwise positions of the respective parts of the subject eye E therefrom. In the anterior segment OCT measurement as above, an A-scan speed is set for example to about 100 kHz.

In the disclosure herein, acquisition of interference signal including position information in the depth direction is termed "A-scan". The "A-scan" in the disclosure herein does not necessarily require dynamic change of a particular configuration in the ophthalmic apparatus disclosed herein. Specifically, the "A-scan" in the disclosure herein may include the following aspects. For example, the "A-scan" may include an aspect that acquires an interference signal including position information at depths in the depth direction by sweeping a wavelength or wave number of light outputted from a light source in SS-OCT (swept-source OCT), an aspect that acquires an interference signal including position information at depths in the depth direction by spectrally diffracting spectrum to decompose the same for each wavelength or for each wave number in SD-OCT (spectral-domain OCT), and an aspect that acquires an interference signal including position information at depths in the depth direction by changing an optical path length of reference light in TD-OCT (time-domain OCT). Further, in the disclosure herein, a number of times the A-scan is repeated per unit time is termed "A-scan speed". For example, in a case where the A-scan is executed 100.000 times per one second, the A-scan speed is 100 kHz.

Next, the processor 200 determines whether the measurement of S34 has been performed for all the scan angles that were preset prior to the measurement (that is, all the incident positions) (S36). In a case where the measurement of S34 has not been performed for all the scan angles (NO to S36), the processor 200 returns to S32 and repeats the processes of S32 to S36. Due to this, the interference signal obtained by the A-scan is obtained for each scan angle scanned by the two-dimensional scanner 108. In this embodiment, the two-dimensional scanner 108 scans in accordance with the A-scan speed (about 100 kHz) of the anterior segment OCT measurement. In the anterior segment OCT measurement, the two-dimensional scanner 108 is scanned such that a B-scan range (width of the B-scan) becomes about 16 mm.

Figure 15:
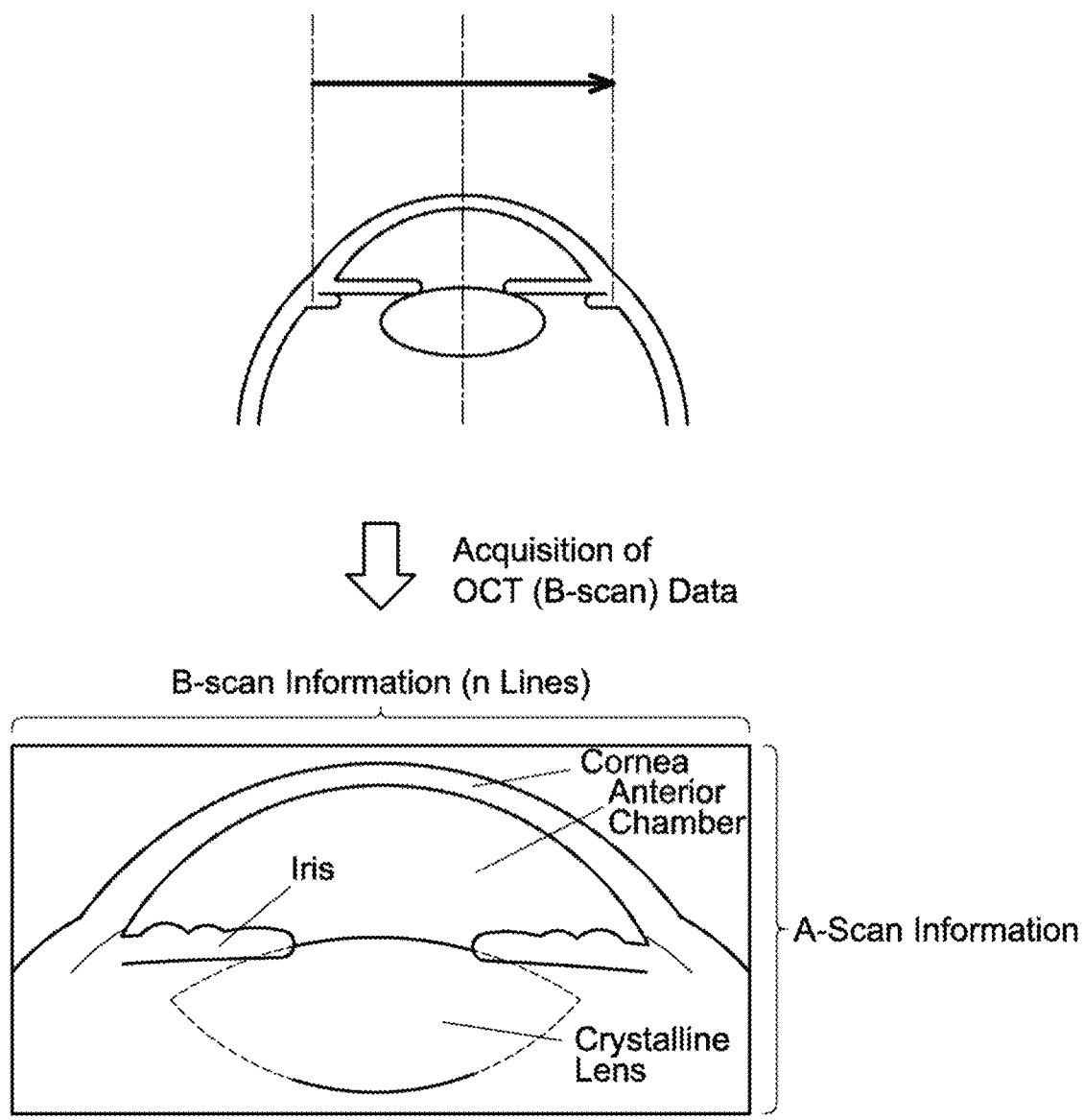
FIG. 15 is a diagram for explaining a procedure for scanning light incident positions on the subject eye within a predetermined range and specifying positions of respective parts of an anterior segment from information obtained for each incident position.

In a case where the measurement of S34 has been performed for all the scan angles (YES to S36), the processor 200 specifies the positions of the respective parts in the subject eye E (such as the anterior and posterior surfaces of the cornea and the anterior and posterior surfaces of the crystalline lens) from the interference signals obtained for the respective scan angles (S38). Specifically, when the process of S34 is performed for each scan angle, the information on the interference signal for this scan angle (A-scan information) is obtained. As such, as shown in FIG. 15, a plurality of two-dimensional information in which multiple pieces of the interference signal information (A-scan information) are arranged is obtained in the number of scan angles (n pieces). Due to this, the processor 200 specifies the positions of the respective parts of the subject eye E (such as the cornea, the anterior chamber, the iris, and the crystalline lens) included in the respective interference signal information by calculating boundaries between those parts of the subject eye E. In the anterior segment OCT measurement, for example, about 800 pieces of A-scan information are obtained in each B-scan. As such, in each B-scan, two-dimensional information in which about 800 pieces of interference signal information (A-scan information) are arranged is obtained.

Figure 16A:
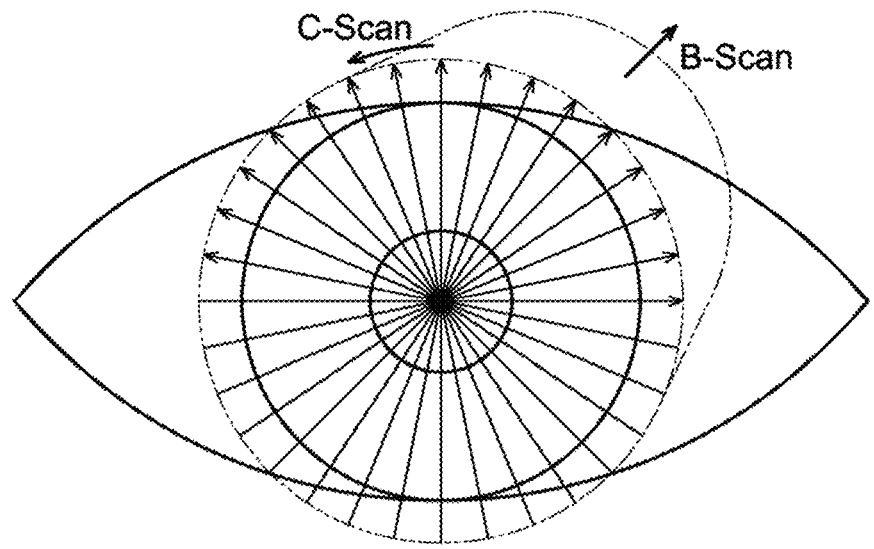
FIG. 16A is a diagram for explaining a radial scanning scheme in anterior segment OCT measurement.
Figure 16B:
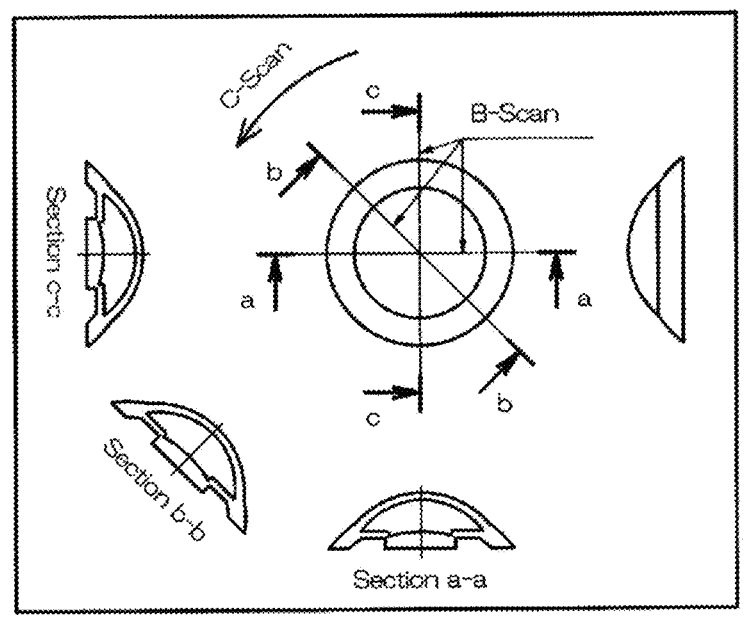
FIG. 16B is a diagram for explaining the radial scanning scheme in anterior segment OCT measurement.

In this embodiment, the anterior segment OCT measurement in S14 is performed with a radial scan scheme as shown in FIG. 16. Due to this, the tomographic images of the anterior segment are acquired over the entire region. That is, the tomographic images are captured with a B-scan direction set in radial directions from the corneal apex of the subject eye E and a C-scan direction set as the circumferential direction about the corneal apex. The processor 200 stores data of the acquired (captured) tomographic images in the memory.

As described above, the anterior segment OCT optical system performs the telecentric scan. Due to this, tomographic images with less distortion can be obtained in the anterior segment OCT measurement. Further, in the anterior segment OCT optical system, the fiber end surface in the fiber collimator 102 is arranged at the position conjugate with the anterior segment of the subject eye E and the anterior segment light source 12 outputs the light with the suitable wavelength for capturing the tomographic images of the anterior segment of the subject eye E. Due to this, the shape of the anterior segment of the subject eye E can suitably be calculated in the anterior segment OCT measurement.

Next, the fundus OCT measurement will be described. As described above, the fundus OCT measurement is performed simultaneously with the anterior segment OCT measurement (S18). As such, the fundus OCT measurement is also performed in accordance with the flowchart shown in FIG. 13, similar to the anterior segment OCT measurement. Specifically, the processor 200 turns on the fundus light source 62 along with the anterior segment light source 12 to cause the light from the fundus light source 62 to enter the subject eye E at the incident position and the incident angle corresponding to the scan angle set in S32 as aforementioned, and intakes the interference signals of the light split by the wavenumber spectrum (S34). In the fundus OCT measurement, the A-scan speed is set to about 10 kHz, for example. Further, in the fundus OCT measurement, the two-dimensional scanner 108 is scanned so that the B-scan range becomes 3.8 mm, for example. As will be described later, in this embodiment, a position of a central fovea is specified from the tomographic images of the fundus of the subject eye E in the processes of calculating the axial length of the subject eye E and specifying a gaze direction of the subject. Due to this, in considering that a general diameter of a macula in the fundus of the subject eye E is about 2 mm, the B-scan range may be set to 2 mm or more.

Figure 17:
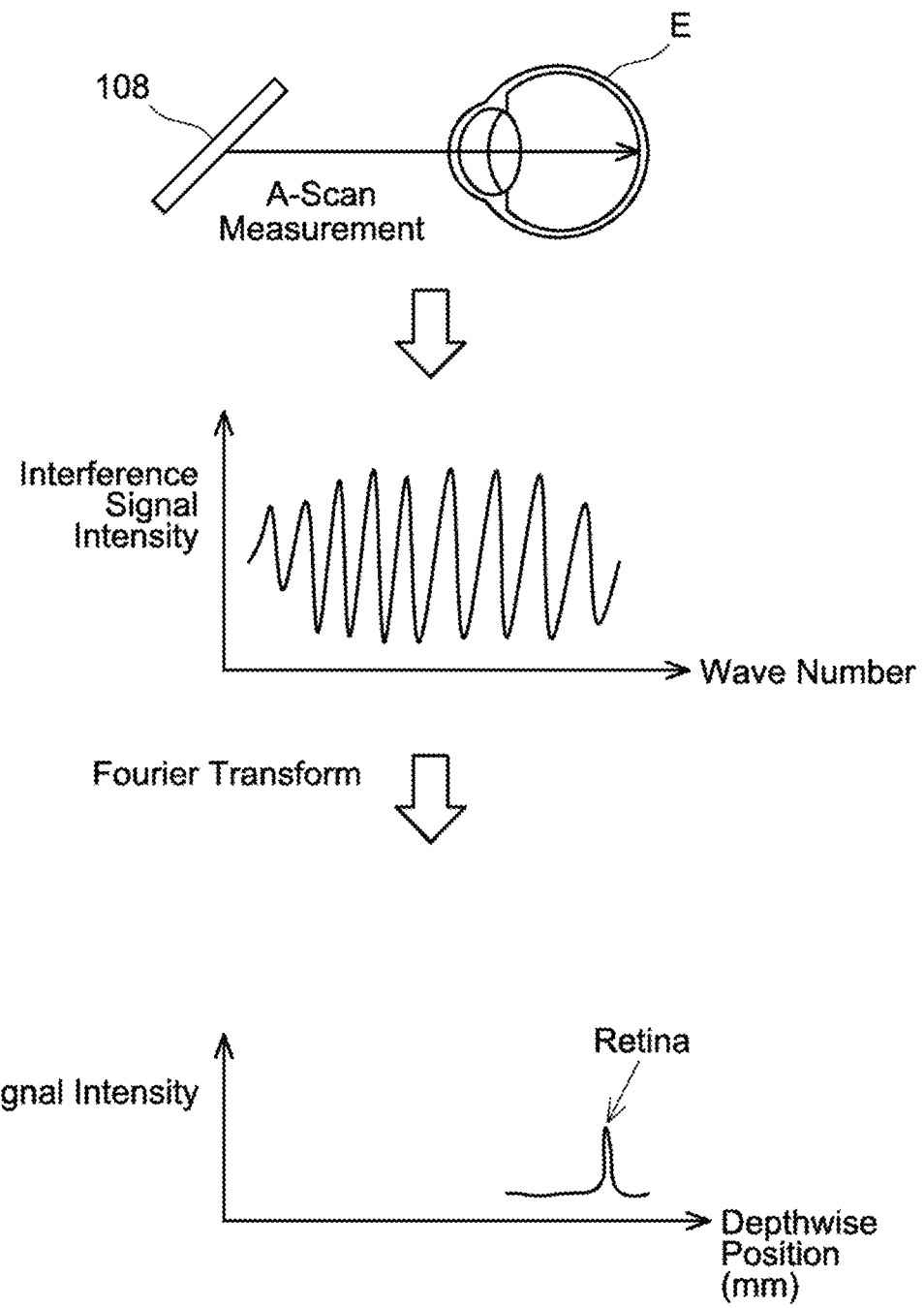
FIG. 17 is a diagram for explaining a procedure for scanning light incident positions on the subject eye within a predetermined range and specifying positions of respective parts of a fundus from information obtained for each incident position.
Figure 18:
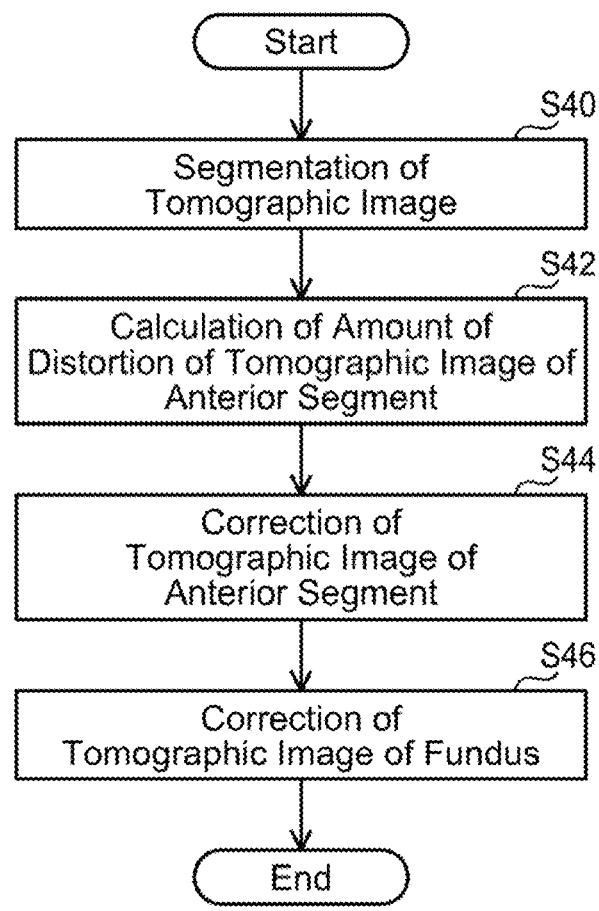
FIG. 18 is a flowchart showing processes of correcting tomographic images.

Further, when the measurement is completed for all the scan angles (YES to S36), the processor 200 specifies the positions of the respective parts of the subject eye E (such as the retina and the choroid) from the interference signals obtained for the respective scan angles as similar to S38 above. Specifically, similar to the anterior segment OCT measurement, a plurality of two-dimensional information in which multiple pieces of the interference signal information (A-scan information) are arranged is obtained in the number of scan angles (n pieces). Due to this, as shown in FIG. 17, the processor 200 specifies the positions of the respective parts of the subject eye E (such as the retina and the choroid) by calculating boundaries of the respective parts of the subject eye E included in each piece of the interference signal information.

Further, in the present embodiment, the fundus OCT measurement in S14 is performed with the radial scan scheme similar to the anterior segment OCT measurement (see FIG. 16). Due to this, the tomographic images of the fundus are acquired over the entire region. In this embodiment, the tomographic images are captured with the B-scan direction set in the radial directions passing through the corneal apex of the subject eye E and the C-scan direction set as the circumferential direction about the corneal apex. The processor 200 stores data of the acquired (captured) tomographic images in the memory. As described above, in the fundus OCT optical system, the fundus light source 62 irradiates the light with the wavelength reaching the fundus of the subject eye E, and the respective optical members are arranged so that the rays of light irradiated from the fundus light source 62 become parallel to the optical axis of the ophthalmic device 1 (optical path L12) in the subject eye E. That is, the telecentric scan is performed in the fundus OCT optical system as well, and tomographic images with less distortion can be obtained upon capturing the subject eye E.

In the present embodiment, the A-scan in the anterior segment OCT measurement and the A-scan in the fundus OCT measurement are performed simultaneously in the same plane. That is, the light outputted from the fundus light source 62 and the light outputted from the anterior segment light source 12 are scanned simultaneously by the two-dimensional scanner 108 in the same plane. Due to this, in the fundus OCT measurement, about 80 pieces of A-scan information are obtained in each B-scan. Further, in the alignment of S12 as aforementioned, the positions of the two-dimensional scanner 108, and the objective lenses 114, 128 are adjusted based on the focal distances of the objective lens 114 and the objective lens 128 such that the B-scan range in the anterior segment OCT measurement and the B-scan range in the fundus OCT measurement are set to the aforementioned ranges (that is, about 16 mm and about 3.8 mm respectively).

In the present embodiment, as described above, both the anterior segment OCT measurement and the fundus OCT measurement perform the telecentric scans. Due to this, tomographic images with relatively less distortion can be acquired. However, the respective parts in the subject eye E have unique curvatures, thicknesses, and refractive indexes. Due to this, the acquired tomographic images may have different shapes from the actual shapes of the respective pans of the subject eye E. In the present embodiment, in view of such a circumstance, when the processor 200 acquires the tomographic images of the anterior segment and the fundus, it calculates an amount of distortion in the tomographic image of the anterior segment and corrects the tomographic images of the anterior segment and the fundus (S20). Correction of the respective tomographic images will be described with reference to FIG. 18.

Figure 19:
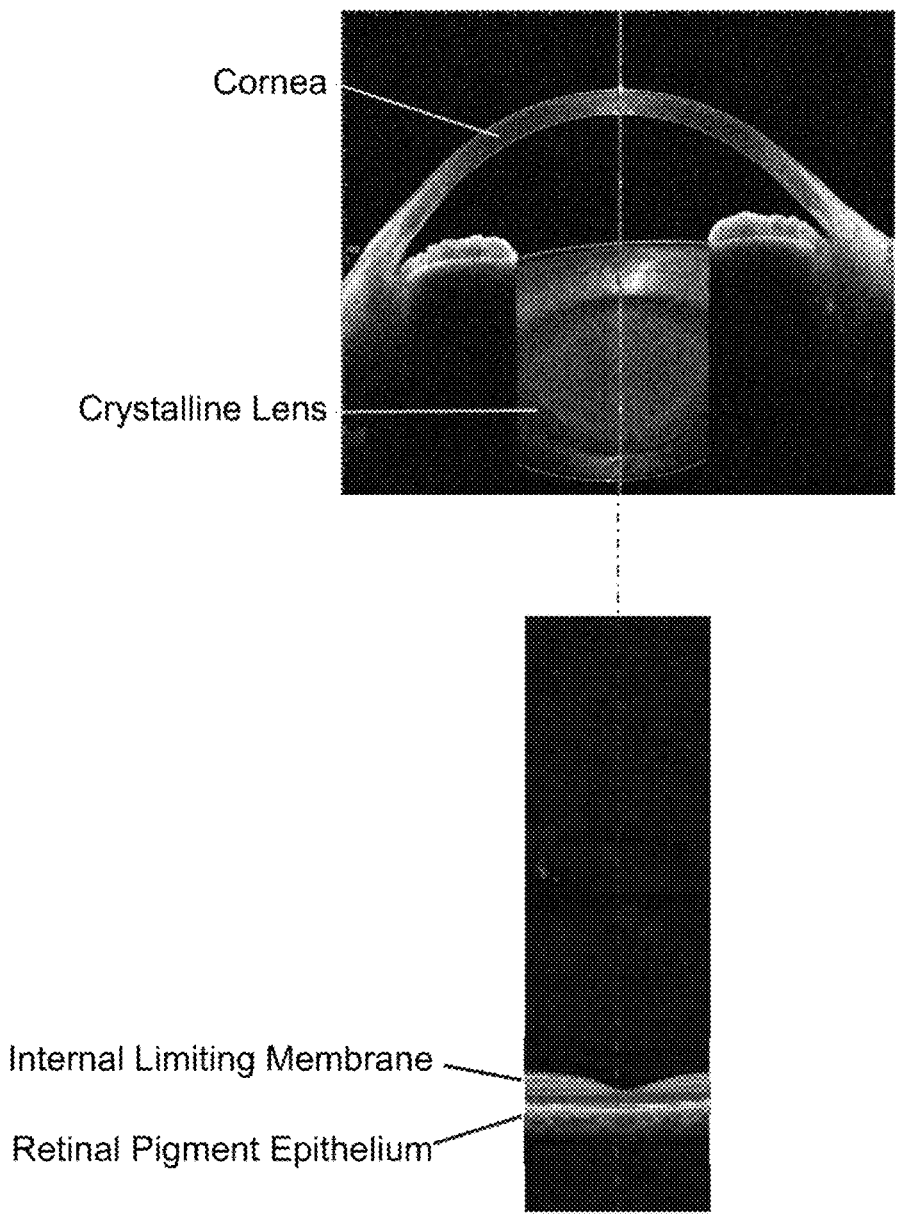
FIG. 19 is a diagram showing tomographic images on which segmentation has been carried out.

The processor 200 firstly performs segmentation on each of the tomographic images of the anterior segment and the fundus acquired in the respective scan angles based on their luminance distribution (S40). Specifically, segmentation on a boundary interface of the cornea and a boundary interface of the crystalline lens is performed on the tomographic image of the anterior segment and segmentation on an internal limiting membrane and a retinal pigment epithelial layer is performed on the tomographic image of the fundus. Due to this, as shown in FIG. 19, tomographic images in which boundary interfaces of the respective parts are defined are obtained. Since known methods can be employed as specific methods of segmentation, thus detailed description thereof will be omitted. If shades are found in a tomographic image of the anterior segment due to opacity in the crystalline lens or the like, the shape of the opaque site may suitably be interpolated after having performed the segmentation on the shapes of the respective parts located around the opaque site.

Figure 20A:
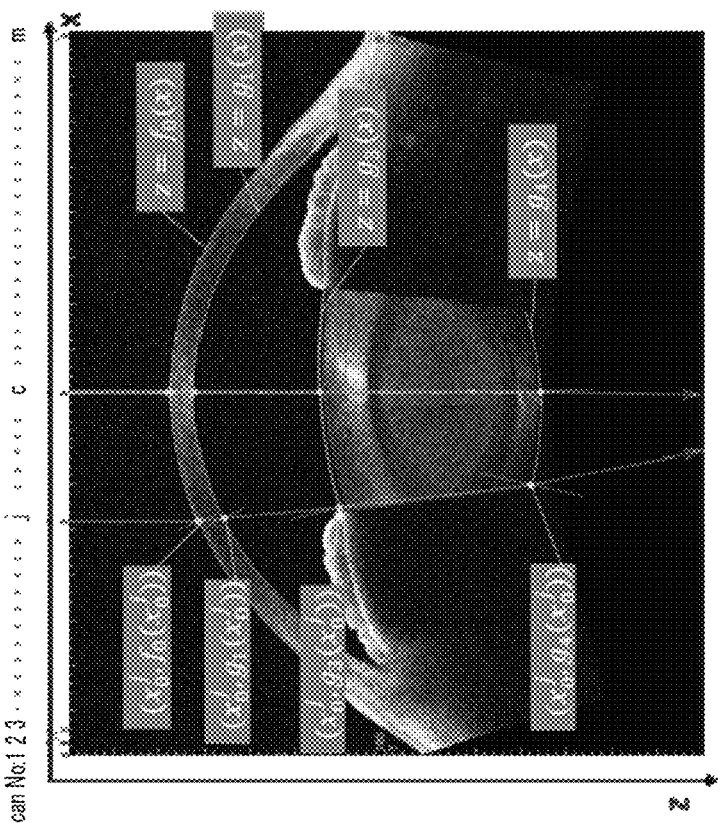
FIG. 20A is a diagram for explaining processes of correcting tomographic images of the anterior segment.

Next, the processor 200 calculates the amount of distortion in the tomographic image of the anterior segment to which the segmentation has been performed (S42). Specifically, the processor 200 firstly maps the respective parts of the anterior segment (the anterior and posterior surfaces of the cornea and the anterior and posterior surfaces of the crystalline lens) in a width direction (x-axis) and a depth direction (z-axis) as shown in FIG. 20(a). Since the anterior segment OCT measurement uses the telecentric scan, m rays of A-scan light enter the anterior segment in parallel by the scan performed by the two-dimensional scanner 108. Further, in tomographic images before correction, each A-scan ray is captured as it is traveling straight within the subject eye E. The processor 200 calculates coordinates of the incident positions of the A-scan rays to the respective parts of the anterior segment (that is, intersections of the A-scan rays and the boundary interfaces of the respective parts of the anterior segment). Then, the processor 200 calculates a function $z=f_i(x)$ for each of the boundary interfaces ($i^{th}$ plane) based on the m sets of coordinates for the boundary interface of each part.

Figure 21:
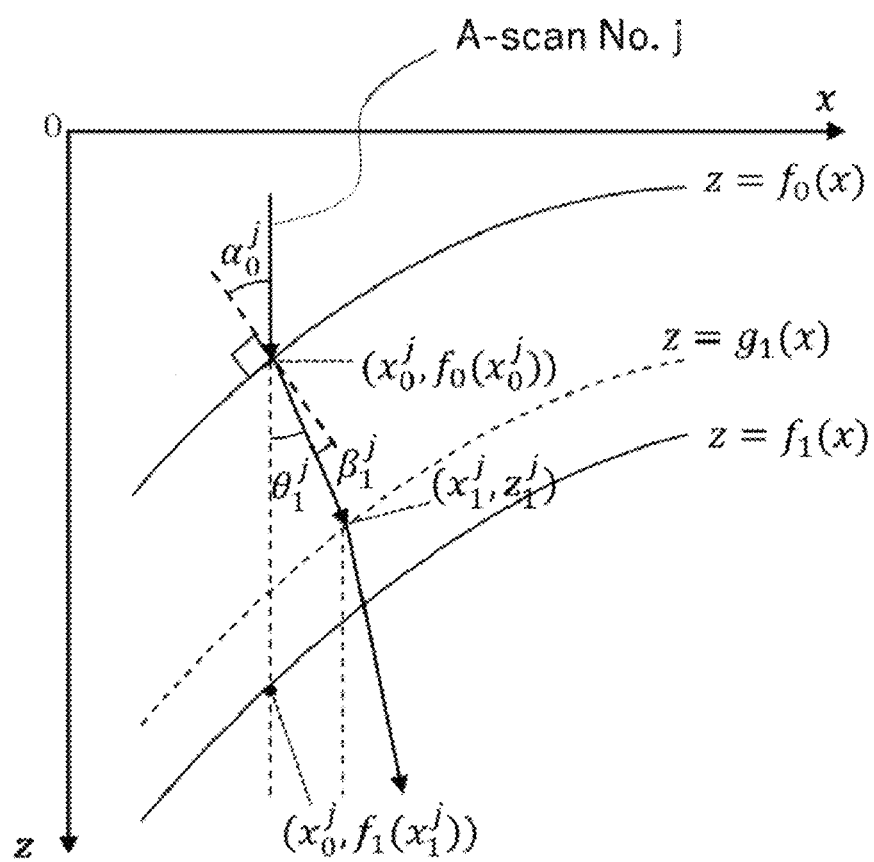
FIG. 21 is a diagram for explaining the processes of correcting tomographic images of the anterior segment.

Next, the processor 200 calculates an actual intersection of the corneal posterior surface ($z=f_i(x)$) being a first plane and a $j^{th}$ A-scan ray within the m rays of A-scan light, with the anterior corneal surface (plane not affected by optical refraction) as a $0^{th}$ plane ($z=f_0(x)$) as shown in FIG. 21 by the following equations (1) and (2) using a known corneal refractive index $n_1$.

[Math 1]

$$x_1^j = x_0^j - \frac{f_1(x_0^j) - f_0(x_0^j)}{n_1} \sin \theta_1^j \quad (1)$$

$$z_1^j = f_0(x_0^j) - \frac{f_1(x_0^j) - f_0(x_0^j)}{n_1} \cos \theta_1^j \quad (2)$$

Here, as shown in FIG. 21, when an angle formed between the A-scan ray and a vertical line relative to a tangential line of the function $z=f_0(x)$ at the incident position of the $j^{th}$ A-scan ray on the anterior corneal surface ($z=f_0(x)$) is termed $\alpha_0^j$, due to $\alpha_0^j$ being a slope of the function $z=f_0(x)$ when $x_0^j$, thus the following equation (3) is established using a differential function $f'_0(x)$ of the function $z=f_0(x)$.

[Math 2]

$$\alpha_0^j = \tan^{-1}\{f'_0(x_0^j)\} \quad (3)$$

Further, based on the Snell's law, a refractive angle $\theta_i^j$ relative to a z-axis (depth direction) can be obtained by the following equations (4) and (5). Here, $n_0$ is a refractive index of air.

[Math 3]

$$\beta_1^j = \sin^{-1}\left\{\frac{n_0 \sin \alpha_0^j}{n_1}\right\} \quad (4)$$

$$\theta_1^j = \alpha_0^j - \beta_1^j \quad (5)$$

Figure 20B:
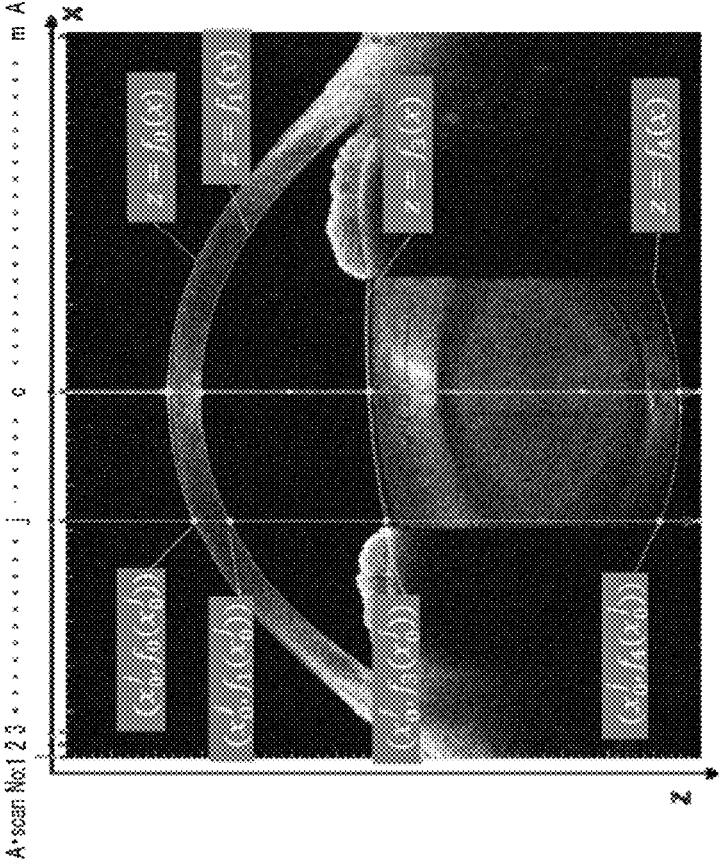
FIG. 20B is a diagram for explaining processes of correcting tomographic images of the anterior segment.

From the above, the processor 200 can obtain the intersection ($x_i^j$, $z_i^j$) of the posterior corneal surface being the first plane and the $j^{th}$ A-scan ray. Similarly, the processor 200 obtains intersections of the posterior corneal surface and all of the A-scan rays (that is, first to $m^{th}$ rays) and thereby calculates the amount of distortion. After this, the processor 200 can obtain a function $z=g_1(x)$ representing the corrected shape of the posterior corneal surface (first plane) as shown in FIG. 20(b) by performing known approximation such as polynomial approximation or spline curve.

The processor 200 obtains functions representing the corrected shapes for all the planes by sequentially performing the aforementioned processes between an $i^{th}$ plane and an $i+1^{th}$ plane. That is, the processes that obtain the function representing the corrected shape of the $i+1^{th}$ plane by using the post-correction function of the $i^{th}$ plane are repeated, and the function $z=g_i(x)$ representing the corrected shape is obtained for every plane. By doing so, the processor 200 corrects the tomographic image of the anterior segment acquired in the OCT measurement (S44). As a result, a tomographic image with the shape of the anterior segment closer to the actual shape can be acquired.

In this embodiment, the refractive angle relative to the depth direction is calculated based on a phase refractive index related to the Snell's law, however, a group refractive index related to traveling speed of light may be used. For example, the Snell's law may be applied to the refractive angle relative to the depth direction and the group refractive index may be applied to the calculation of the coordinates of the intersections of the A-scan rays and the boundary interfaces of the respective parts of the subject eye E. In such a configuration, the accuracy can further be improved.

Next, the processor 200 corrects the tomographic image of the fundus based on the corrected tomographic image of the anterior segment (S46). Here, as aforementioned, the zero-point adjusting mechanism is arranged in the anterior segment OCT optical system and the fundus OCT optical system. Further, a distance between the zero-point position (position where the measurement optical path length and the reference optical path length match) in the anterior segment OCT optical system and the zero-point position in the fundus OCT optical system is a fixed value $\Delta L$ as shown in FIG. 22. As such, when the respective zero-points are set as shown in FIG. 22(a), a depthwise coordinate $z_R$ in the tomographic image of the fundus can be represented as $z_R + \Delta L$, where the zero-point in the tomographic image of the anterior segment is regarded as the origin. That is, the coordinate system of the tomographic image of the anterior segment can be applied to the coordinates in the tomographic image of the fundus.

Further, as described above, in the embodiment, the light outputted from the anterior segment light source 12 and the light outputted from the fundus light source 62 are scanned in all of the B-scans in which the rays are scanned radially such that they pass through the corneal apex. In other words, the B-scan center axis matches between the anterior segment OCT measurement and the fundus OCT measurement. That is, the ray passing through the center axis included in the light outputted from the anterior segment light source 12 travels on the same optical path as the ray passing through the center axis included in the light outputted from the fundus light source 62. Due to this, by tracking the optical path passing through the center axis of the B-scan, the tomographic image of the fundus can thereby be corrected. In the present embodiment, since the A-scan speed is different between the anterior segment OCT measurement and the fundus OCT measurement, the numbers of A-scan information in each B-scan differ, however, the following description will be given by assuming that the ray passing through the center axis of the B-scan is a $c^{th}$ ray included in the m rays of A-scan light, similar to the case with the anterior segment OCT measurement, for the sake of convenience.

Specifically, a coordinate of an intersection of the internal limiting membrane and the $c^{th}$ ray of A-scan light in the tomographic image of the fundus can be obtained by the following equations (6) to (10) similar to the processes of calculating the amount of distortion in the tomographic image of the anterior segment. Here, $n_3$ is the refractive index of the crystalline lens and $n_4$ is a refractive index of a vitreous body.

[Math 4]

$$x_4^c = x_3^j - \frac{f_4(x_0^c) - g_3(x_0^c)}{n_4} \sin\theta_4^c \quad (6)$$

$$z_4^c = f_3(x_0^c) - \frac{f_4(x_0^c) - g_3(x_0^c)}{n_4} \cos\theta_4^c \quad (7)$$

$$\alpha_3^c = \tan^{-1}\{g_3'(x_0^c)\} - \theta_3^c \quad (8)$$

$$\beta_4^c = \sin^{-1}\left\{\frac{n_3 \sin\alpha_3^c}{n_4}\right\} \quad (9)$$

$$\theta_4^c = \theta_3^c + \alpha_3^c - \beta_4^c \quad (10)$$

In this embodiment, the fundus OCT measurement performs the telecentric scan. That is, the A-scan rays other than the $c^{th}$ ray are also parallel to the $c^{th}$ ray of A-scan light. Due to this, a tomographic image with a closer shape to the actual shape can be acquired as shown in FIG. 22(b) by changing a magnification of the size on the fundus side of the posterior surface of the crystalline lens to $1/n_4$ in a tomographic image of an eye that combined the tomographic images acquired respectively by the anterior segment OCT measurement and the fundus OCT measurement, and then rotating the image by the angle calculated as above with the intersection of the $c^{th}$ ray of A-scan light and the posterior surface of the crystalline lens as the center.

In this embodiment, the wavelengths are different in the anterior segment light source 12 and the fundus light source 62. Due to this, strictly speaking, the refractive indexes of the respective parts of the subject eye E differ due to wavelength scattering. To address this, the optical path of the $c^{th}$ ray of A-scan light may be re-tracked based on the refractive index corresponding to the wavelength of the fundus light source 62 after having corrected the tomographic image of the anterior segment. In such a configuration, the tomographic image of the fundus with even improved accuracy can be acquired.

Further, in this embodiment, the refractive index of the crystalline lens is set based on the known value, however, the refractive index of the crystalline lens of the subject eye may differ depending on the age and the level of opacity in the crystalline lens. For example, a nucleus of the crystalline lens may have stronger opacity and greater refractive index with age. Due to this, the refractive index to be set may suitably be changed according to the age of the subject and the level of opacity in the crystalline lens. In such a configuration, the tomographic image of the eye can be acquired with improved accuracy. Further, in the present embodiment, the correction on the tomographic images was performed by assuming that the refractive index of the crystalline lens is uniform within the crystalline lens, however, the nucleus of the crystalline lens may be segmented by image luminance, and different refractive indexes may be set to each of lens cortex and the nucleus of the crystalline lens. In such a configuration, the tomographic image of the eye can be acquired with improved accuracy.

Further, in the embodiment, since the fundus OCT optical system performs the telecentric scan, the tomographic image of the fundus is corrected by tracking only the optical path of the light ($c^{th}$ ray) passing through the center axis of the B-scan. However, for example, the tomographic image of the fundus may be corrected by tracking the optical path for all of the A-scan rays. In such a configuration, the tomographic image of the eye with even more improved accuracy can be acquired.

Figure 23A:
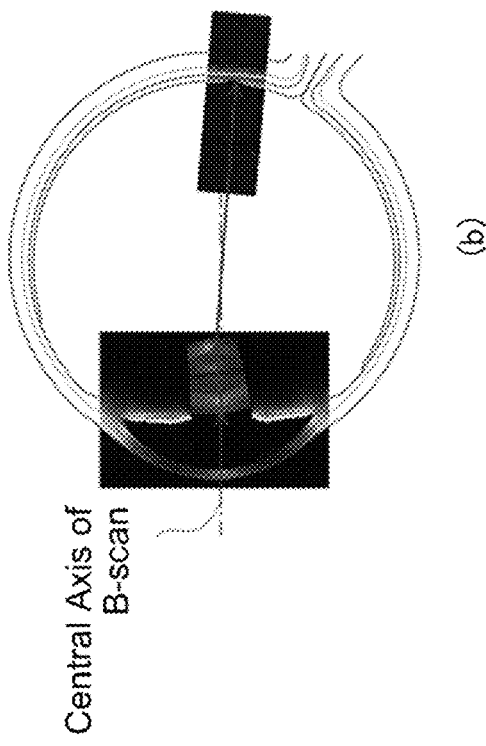
FIG. 23A is a diagram for explaining processes of calculating an eye axial length.
Figure 23B:
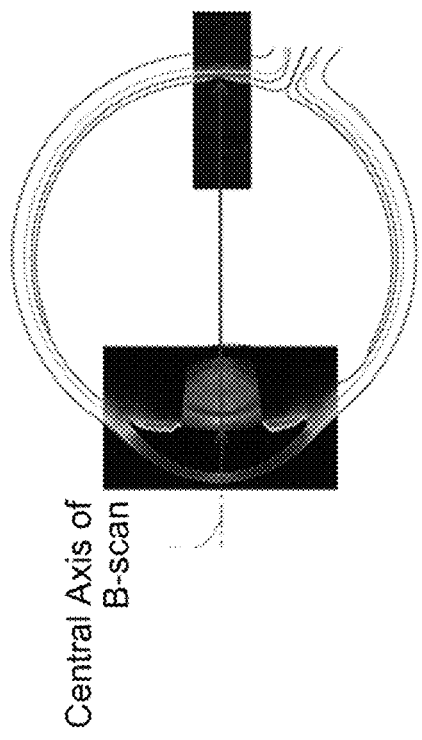
FIG. 23B is a diagram for explaining processes of calculating the eye axial length.

As described above, once the processor 200 corrects the tomographic images, it calculates the eye axial length (S22 of FIG. 12). Specifically, as shown in FIG. 23, it measures the distance from the cornea to the retinal pigment epithelial layer (more specifically, the central fovea) along the center axis of the B-scan. FIG. 23(a) shows a post-correction tomographic image in a cross section in which light refraction is relatively small in the anterior segment, and FIG. 23(b) shows a post-correction tomographic image in a cross section in which the light refraction is relatively large in the anterior segment. The processor 200 measures this distance for each tomographic image in all the B-scans that were scanned radially, and calculates an average value of the distances as the eye axial length. In this embodiment, since the light passing through the center axis of the B-scan in every scan angle passes through the same optical path, the eye axial length with a very small influence of segmentation error can be calculated by averaging the distances in all the scan angles. When there is a tomographic image with a large segmentation error due to the influence of opacity and the like in the crystalline lens, the processor 200 may exclude this tomographic image with the large error based on the segmentation results of the tomographic images in other scan angles.

Next, the processor 200 calculates a three-dimensional inclination of the center axis from the posterior surface of the crystalline lens to the central fovea in each tomographic image, and determines whether the calculated inclination is greater than a predetermined threshold (S24). For example, in the tomographic image in the example shown in FIG. 23(a), the inclination is calculated as 0°, and in the tomographic image in the example shown in FIG. 23(b), the inclination is calculated as 3°. In a case where the calculated inclination is greater than the predetermined threshold (such as 5°) (YES to S24), the processor 200 warns that reliability of the calculated eye axial length is low and thus an expected effect might not be achieved by a cataract surgery (S26). This warning is performed for example by an output to the touch panel monitor 174.

When all the measurements (the refraction measurement, the anterior segment OCT measurement, and the fundus OCT measurement) are completed, the processor 200 outputs the analysis results to the touch panel monitor 174 (S28). Since the ophthalmic device 1 of the present embodiment can execute plural types of measurements, namely the anterior segment OCT measurement, the fundus OCT measurement, and the refraction measurement, it can comprehensively analyze the state of the subject eye E. By executing the measurements on the subject eye E before a cataract surgery, Intraocular lens (IOL) power calculation, cornea aberration, and opaque state of the crystalline lens can be calculated as the analysis results, for example. Further, by executing the measurements on the subject eye E before the cataract surgery, errors with respect to postoperative refractivity of the subject eye E that is predicted before the surgery can be evaluated, and this can be used to improve accuracy of the IOL power calculation. Further, by executing the measurements on a subject eye suffering glaucoma, progression of the glaucoma can be predicted from a retina thickness distribution in the fundus, and a closure angle thereof may be screened. Further, by executing the measurements on an excessively-myopia subject of the subject eye, the state of the subject eye can be examined in detail and comprehensively.

Figure 24:
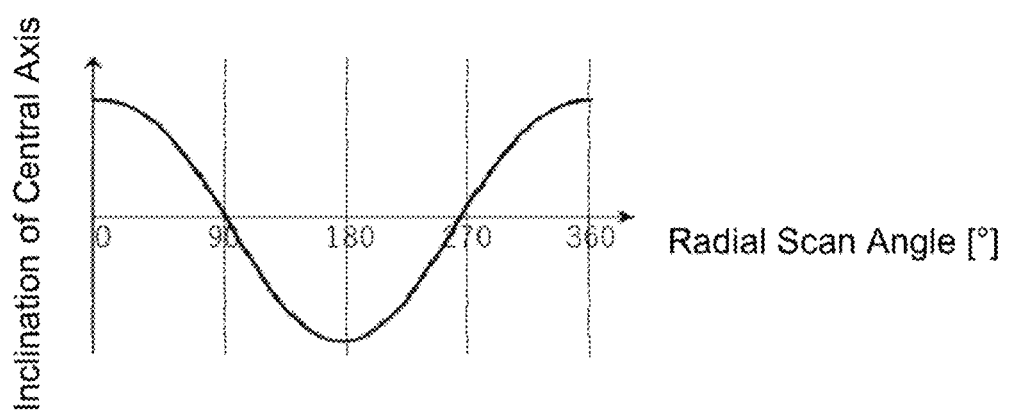
FIG. 24 is a diagram showing an example of a relationship between an inclination of a center axis and a scan angle of a B-scan.
Figure 25:
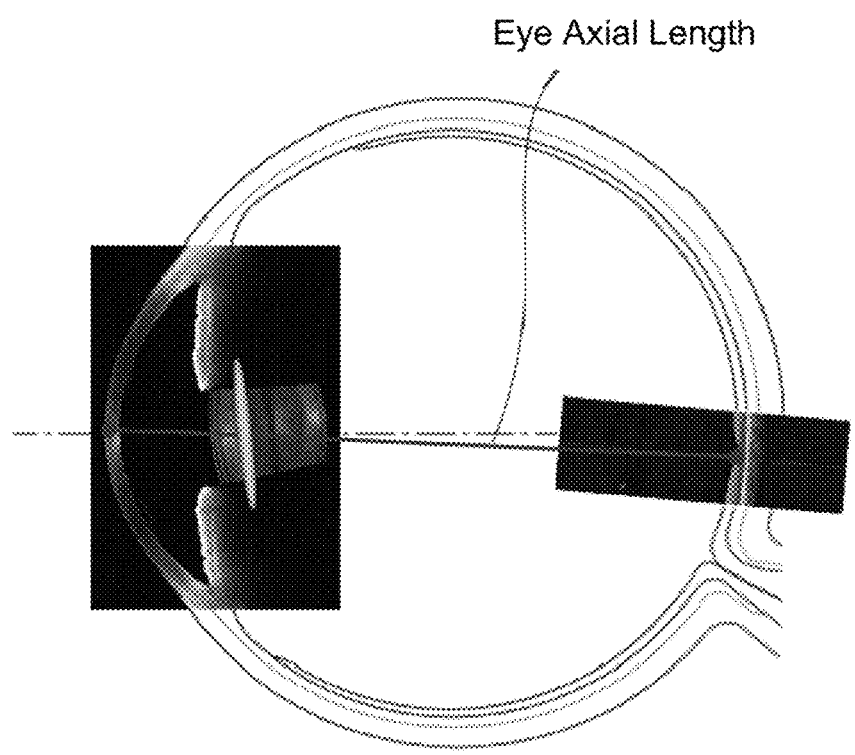
FIG. 25 is a diagram for explaining processes of calculating an eye axial length with an influence of gaze fixation displacement having been corrected.

As shown in FIG. 24, there may be a case in which the inclination of the line connecting the posterior surface of the crystalline lens and the central fovea (inclination calculated in S24) changes due to the radial scan angle (angular position in the circumferential direction about the corneal apex). In the example shown in FIG. 24, a state in which the scan angle relative to the subject eye E is horizontal is expressed as 0°. Here, the processor 200 may extract a tomographic image that was acquired with the scan angle with the largest inclination (such as the radial scan angle 0° in FIG. 24), and calculate the distance of the line connecting the cornea and the central fovea of this tomographic image as the eye axial length as shown in FIG. 25. When the eye axial length is calculated as above, even when the gaze of the subject is displaced during the examination due to the gaze fixation displacement, the eye axial length that corrected the influence thereof (that is, on the axis approximate to an axis of vision) can be calculated. Further, since IOL power calculation is performed by predicting a postoperative state (such as IOL fixation position, axial length, and corneal shape) of the subject eye E after the cataract surgery, the eye axial length calculated as above is substantially equal to being an eye axial length of a postoperative state in which the crystalline lens is absent, thus it is very useful to calculate this eye axial length.

Figure 26:
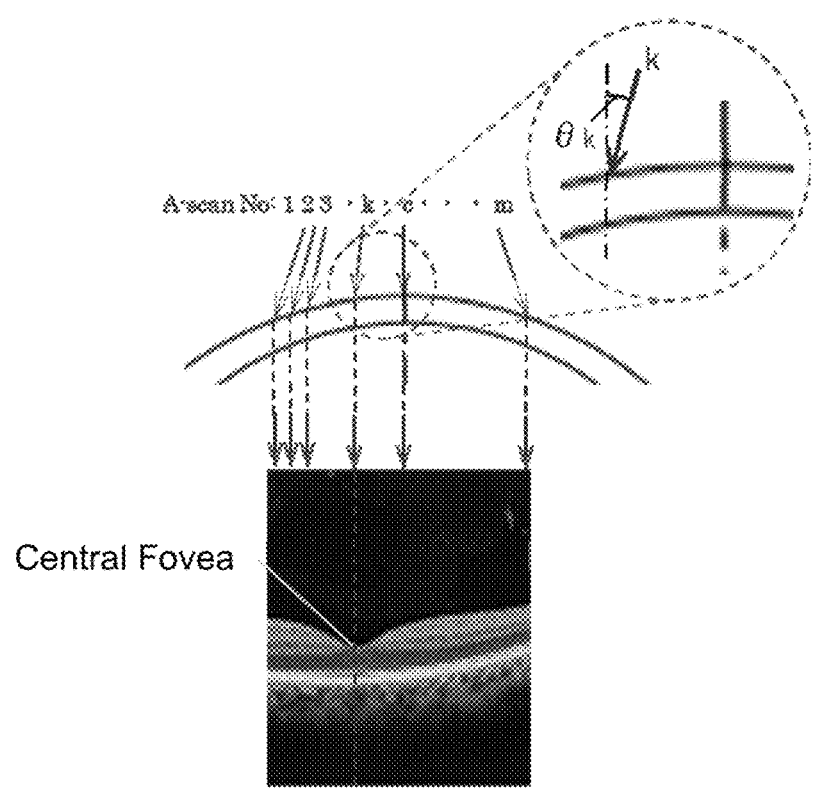
FIG. 26 is a diagram for explaining processes of specifying a gaze direction
Figure 27:
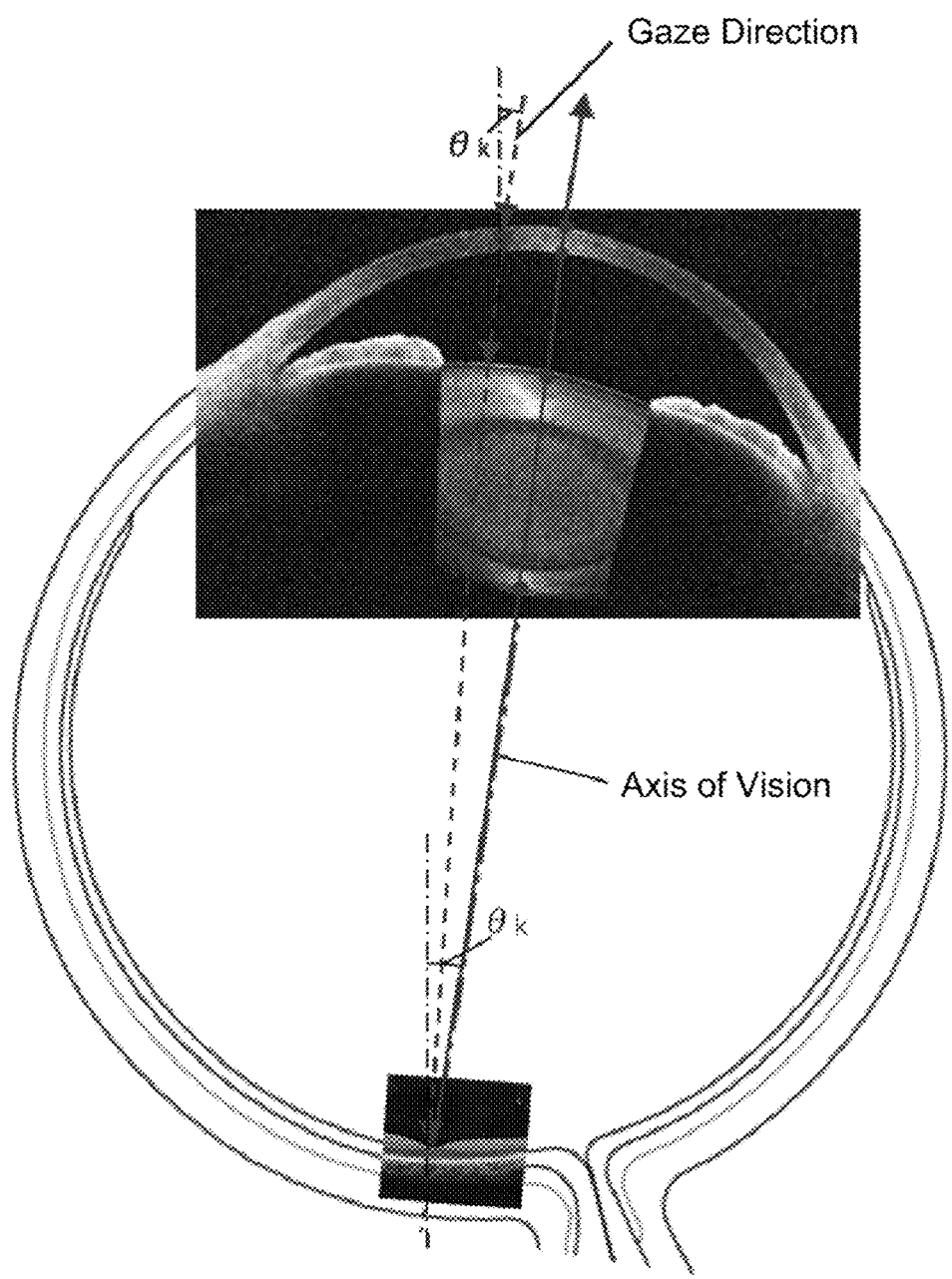
FIG. 27 is a diagram for explaining processes of specifying the gaze direction.

Further, in the eye axial length calculation, the processor 200 may calculate the distance along the axis of vision from the central fovea to the cornea as the eye axial length as described below. The processor 200 firstly specifies the gaze direction of the subject eye E. Specifically, as shown in FIG. 26, the processor 200 specifies the position of the central fovea from the pre-correction tomographic image of the fundus. Then, the processor 200 specifies the order of the A-scan ray irradiated to the specified central fovea among the m rays of A-scan light. By specifying that $k^{th}$ ray of A-scan light is the light irradiated to the central fovea, the processor 200 can specify the incident angle $\theta_k$ of the A-scan ray to the anterior corneal surface, that is, the gaze direction of the subject eye E. After having specified the gaze direction of the subject eye E, the processor 200 specifies the position of the central fovea from the corrected tomographic image of the fundus as shown in FIG. 27. Then, the processor 200 uses the corrected tomographic images of the anterior segment and the fundus to reverse-track the optical paths in a direction parallel to the specified gaze direction from the position of the central fovea toward the anterior corneal surface. By doing so, the axis of vision of the subject eye E can be specified. The processor 200 may calculate the distance from the central fovea to the anterior corneal surface along the specified axis of vision as the eye axial length.

As described above, in the ophthalmic device 1 of the embodiment, firstly the amount of distortion in the tomographic image of the anterior segment acquired by the anterior segment OCT measurement is calculated, and the tomographic image of the anterior segment is thereby corrected. Here, in this embodiment, the light outputted from the anterior segment light source 12 and the light outputted from the fundus light source 62 are scanned simultaneously in the same plane. That is, in this ophthalmic device 1, the tomographic images of the anterior segment and the fundus indicating the cross section in the same plane of the subject eye E are acquired. As such, the amount of distortion in the tomographic image of the anterior segment can be used in correcting the tomographic image of the fundus. Due to this, the tomographic image of the fundus can be corrected based on the amount of distortion in the tomographic image of the anterior segment (that is, the corrected tomographic image of the anterior segment). As above, in this ophthalmic device 1, the correction of the tomographic image of the anterior segment and the tomographic image of the fundus can be performed by calculating the amount of distortion in the tomographic image of the anterior segment without requiring complicated processes.

If the gaze fixation direction of the subject is tilted relative to the optical axis of the ophthalmic device 1, the central fovea may not be captured in the tomographic image in a B-scan direction that differs from this tilted gaze fixation direction. However, in this embodiment, the B-scans are performed radially at multiple positions along the circumferential direction about the corneal apex. Due to this, at least one of those B-scan directions would be a direction matching the gaze fixation direction. As such, by acquiring the tomographic image in the B-scan direction matching the gaze fixation direction, the position of the central fovea can be specified. In this case, the gaze direction of the subject can be specified based on the B-scan direction of the tomographic image in which the central fovea was detected and the position of the central fovea.

(Corresponding Relationship)

The anterior segment light source 12 and the fundus light source 62 are respectively an example of "first light source" and "second light source". The measurement interference light in the anterior segment OCT measurement and the measurement interference light in the fundus OCT measurement are respectively an example of "first interference light" and "second interference light". The range including the anterior segment and the range including the fundus are respectively an example of "first range" and "second range". The B-scan is an example of "specific scan". The corneal apex and the central fovea are respectively an example of "specific position" and "specific part". The two-dimensional scanner 108 is an example of "scanner".

The above-described embodiment exemplifies the examinations for the ranges including the anterior segment and the fundus of the subject eye E, however, they are not limited thereto. For example, ranges including the other parts of the subject eye E may be examined by suitably adjusting the central wavelengths of the light outputted from the light sources 12, 62 and/or by suitably changing the configuration of the probe optical system 26.

Further, in the aforementioned embodiment, the two-dimensional scanner 108 was shared by the anterior segment OCT optical system and the fundus OCT optical system, however, no limitation is made to such a configuration. For example, a dedicated two-dimensional scanner may be disposed in the anterior segment OCT optical system and another dedicated two-dimensional scanner may be disposed in the fundus OCT optical system.

Further, as described above, a lens array having a large number of fine lenses arranged in a matrix pattern may be disposed instead of the donut lens 138 in the refractometric measurement optical system. In such a configuration, when light is irradiated to the lens array, the rays in the same number as the fine lenses are irradiated to the two-dimensional sensor 140 by the fine lenses. When light with a distorted wave surface is irradiated to the lens array, a ray with a displaced optical axis is irradiated from the lens at the position corresponding to the position of this distortion among the fine lenses to the two-dimensional sensor 140. That is, by arranging the lens array between the lens 136 and the two-dimensional sensor 140, a same function as a wave surface sensor optical system can be given to the refractometric measurement optical system. Due to this, in the refractometric measurement optical system, not only the total refractivity of the subject eye E but also total aberration of the subject eye E can be measured, and information related to the refraction of the subject eye E can be measured in greater detail.

Further, in the above-described embodiment, the light outputted from the fundus light source 62 is used in the measurement of the refractivity of the subject eye E. However, a light source different from the fundus light source 62 may be used for the measurement of the refractivity of the subject eye E. In this case, the different light source may output light with a wavelength that differs from those of the light outputted from the anterior segment light source 12 and the fundus light source 62, and for example, it may output light with a central wavelength of 0.70 μm or more and 0.95 μm or less. The light with the wavelength of 0.70 m or more and 0.95 μm or less has a high intraocular penetration rate. Further, the light with the wavelength of 0.70 μm or more and 0.95 μm or less has a low relative visibility to the subject eye E, so the light is less likely to make the subject feel brightness as well as is suitable for visual function evaluation because it is close to visible light. As such, by using the light with the wavelength of 0.70 μm or more and 0.95 μm or less in the measurement of the refractivity, the light from the light source can sufficiently be provided to the fundus of the subject eye E and the light with the suitable wavelength for measuring the refractivity of the subject eye E can be outputted.

While specific examples of the present disclosure have been described above in detail, these examples are merely illustrative and place no limitation on the scope of the patent claims. The technology described in the patent claims also encompasses various changes and modifications to the specific examples described above. The technical elements explained in the present description or drawings provide technical utility either independently or through various combinations. The present disclosure is not limited to the combinations described at the time the claims are filed. Further, the purpose of the examples illustrated by the present description or drawings is to satisfy multiple objectives simultaneously, and satisfying any one of those objectives gives technical utility to the present disclosure.

What is claimed is:

1. An ophthalmic device comprising:
    a first light source configured to output first light with which a subject eye is irradiated;
    a second light source configured to output second light with which the subject eye is irradiated;
    a first interferometer configured to acquire a first tomographic image of a first range of the subject eye based on first interference light obtained from reflected light of the first light;
    a second interferometer configured to acquire a second tomographic image of a second range of the subject eye based on second interference light obtained from reflected light of the second light, the second range being different from the first range; and
    a controller,
    wherein
    the controller is configured to:
        perform a specific scan on the subject eye that scans the first light and the second light simultaneously in a same plane, wherein the first tomographic image and the second tomographic image are obtained by performing the specific scan;
        perform the specific scan a plurality of times on the subject eye so that the first light and the second light pass through a specific position of the subject eye;
        perform the respective specific scans radially at different positions in a circumferential direction with the specific position of the subject eye being a center;
        calculate respective incident positions and incident angles of the first light at a plurality of parts included in the first range of the subject eye in the specific scan;
        calculate an amount of distortion of the first tomographic image based on the respective incident positions and incident angles, and respective refractive indexes of the plurality of the parts;
        correct the first tomographic image based on the amount of distortion of the first tomographic image; and
        correct the second tomographic image based on the amount of distortion of the first tomographic image calculated based on the first light having entered the specific position.

2. The ophthalmic device according to claim 1, wherein
a first optical path of the first light and a second optical path of the second light partially overlap,
the ophthalmic device further comprising:
a scanner configured to scan the first light and the second light and arranged in an overlapping section where the first optical path and the second optical path partially overlap, wherein
the controller is configured to perform the specific scan using the scanner.

3. The ophthalmic device according to claim 2, further comprising:
a lens arranged between the scanner and the subject eye, wherein
the first range includes an anterior segment of the subject eye,
the scanner is configured to change an incident position of the first light outputted from the first light source on the subject eye, and
the first light is scanned by the scanner so that traveling directions of the first light entering the subject eye are substantially parallel to each other.

4. The ophthalmic device according to claim 2, wherein
the second range includes a fundus of the subject eye,
the scanner is configured to change an incident position and an incident angle of the second light outputted from the second light source on the subject eye, and
the second light is scanned by the scanner so that traveling directions of the second light entering the subject eye intersect between the scanner and the subject eye and are substantially parallel to each other inside the subject eye.

5. The ophthalmic device according to claim 1, wherein the controller is configured to:
calculate a position of a specific part of the subject eye from the second tomographic image; and
specify a gaze direction of the subject eye based on the position of the specific part.

6. The ophthalmic device according to claim 5, wherein the controller is configured to calculate an angle between an optical axis of light passing through the specific position and the specified gaze direction.

7. The ophthalmic device according to claim 1, wherein the controller is configured to calculate an axial length of the subject eye based on the corrected first tomographic image and the corrected second tomographic image.

\* \* \* \* \*